US008329987B2

(12) United States Patent
Parkash et al.

(10) Patent No.: US 8,329,987 B2
(45) Date of Patent: *Dec. 11, 2012

(54) METAL RESISTANT PLANTS AND METHODS OF MANUFACTURE THEREOF

(75) Inventors: Om Parkash, Amherst, MA (US); Anirudha Dixit, Amherst, MA (US)

(73) Assignee: The University of Massachusetts, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/098,706

(22) Filed: May 2, 2011

(65) Prior Publication Data
US 2011/0271403 A1 Nov. 3, 2011

Related U.S. Application Data

(63) Continuation of application No. 12/125,362, filed on May 22, 2008, now Pat. No. 7,951,992.

(60) Provisional application No. 60/939,751, filed on May 23, 2007.

(51) Int. Cl.
*A01H 5/00* (2006.01)
*A01H 5/10* (2006.01)
*C12N 15/09* (2006.01)
*C12N 15/82* (2006.01)

(52) U.S. Cl. ........ 800/278; 800/298; 800/289; 435/468; 435/69.1

(58) Field of Classification Search .................. None
See application file for complete search history.

(56) References Cited

U.S. PATENT DOCUMENTS

| 7,951,992 B2 * | 5/2011 | Parkash et al. ............... 800/278 |
| 2002/0160378 A1 | 10/2002 | Harper et al. |
| 2005/0198707 A1 | 9/2005 | Meagher et al. |
| 2005/0216976 A1 | 9/2005 | Meagher et al. |
| 2006/0150283 A1 | 7/2006 | Alexandrov et al. |
| 2007/0214517 A1 | 9/2007 | Alexandrov et al. |

FOREIGN PATENT DOCUMENTS

| WO | 8700551 | 1/1987 |
| WO | 0248335 A2 | 6/2002 |
| WO | 2004058963 A2 | 7/2004 |
| WO | 2005070088 A2 | 8/2005 |

OTHER PUBLICATIONS

U.S. Appl. No. 12/034,248 to Parkash; filed Feb. 20, 2008; Title: Metal Resistant Plants, and Methods of Manufacture Thereof.
Altschul et al; "Gapped BLAST and PSI-BLAST: a New Generation of Protein Database Search Programs"; Nucleic Acids Research; 25; pp. 3389-3402; (1997).
Baluska; "Plant Formins Come of Age: Something Special About Cross-Walls"; New Phytologist; 168; pp. 499-503; (2005).
Dhankher; "Arsenic Metabolism in Plants: An Inside Story"; New Phytologist; 168; pp. 503-505; (2005).
Dhankher, et al; "Engineering Tolerance and Hyperaccumulation of Arsenic in Plants by Combining Arsenate Reductase and Y-Glutamylcysteine Synthetase Expression"; Nature Biotechnology; 20; pp. 1140-1145; (2002).
Dhankher, et al; Hyperaccumulation of Arsenic in the Shoots of *Arabidopsis* Silenced for Arsenate Reductase (ACR2); PNAS; 103; pp. 5413-5418; (2006).
Karlin, et al; "Methods for Assessing the Statistical Significance of Molecular Sequence Features by Using General Scoring Schemes"; PNAS; 87; pp. 2264-2268; (1990).
Li et al; "Arsenic and Mecury Tolerance and Cadmium Sensitivity in *Arabidopsis* Plants Expressing Bacterial y-Glutamylcysteine Synthetase"; Environmental Toxicology and Chemistry; 24; pp. 1376-1386; (2005).
Pannell; "Phenotypic Plasticity and a Functional VS Genetic Perspective of Plant Gender"; New Phytologist; 168; pp. 506-510; (2005).
Williams et al; "Variation in Arsenic Speciation and Concentration in Paddy Rice Related to Dietary Exposure"; Environ. Sol. Technol.; 39; pp. 5531-5540; (2005).
International Search Report and Written Opinion; International Application No. PCT/US2008/002181; International Filing Date Feb. 20, 2008; Date of Mailing Jun. 25, 2008; 16 pages.
Altschul, et al.; "Basic Local Alignment Search Tool"; J. Mol. Biol.; 215; pp. 403-410; (1990).
Jin, et al.; "Phylogenetic and Expression Analysis of ZnF-AN1 Genes in Plants"; Genomics; 90; pp. 265-275; (2007).
Saurin, et al.; Does This Have a Familiar Ring?; Trends Biochem. Sci.; 21; pp. 208-214; (1996).
Sok, et al.; "Rsenite-Inducible RN-Associated Protein ( IR P) Protects Cells From Arsenite Toxicity"; Cell Stress & Chaperones; 6; pp. 6-15; (2001).
Vij, et al.; "Genome-wide Analysis of the Stress Associated Protein (SAP) Gene Family Containing A20/AN1 Zinc-Finger(s) in Rice and Their Phylogenetic Relationship With *Arabidopsis*"; Mol. Gen. Genomics; 276; pp. 565-575; (2006).
International Search Report ; International Application No. PCT/US2008/064520; International Filing Date May 22, 2008; Date of Mailing Apr. 14, 2009; 8 pages.

(Continued)

*Primary Examiner* — Medina A Ibrahim
(74) *Attorney, Agent, or Firm* — Cantor Colburn LLP

(57) ABSTRACT

Disclosed herein is a transgenic plant transformed with an isolated nucleic acid comprising a plant arsenite-inducible RNA-associated protein coding sequence operatively linked to a plant-expressible transcription regulatory sequence, wherein the plant arsenite-inducible RNA-associated protein (AIRAP) coding sequence encodes a polypeptide that is at least 95% identical to a polypeptide sequence of SEQ ID NO:8, SEQ ID NO:9, SEQ ID NO:10, SEQ ID NO:11, SEQ ID NO:12, SEQ ID NO:13, or SEQ ID NO:14, wherein the plant arsenite-inducible RNA-associated protein coding sequence encodes a polypeptide that confers resistance to an environmental stress, wherein greater than or equal to about 25% of transgenic plants are resistant to an environmental stress, and wherein the environmental stress inhibits the growth of wild type plants.

20 Claims, 15 Drawing Sheets

OTHER PUBLICATIONS

Eapen et al.; "Prospects of Genetic Engineering of Plants for Phytoremediation of Toxic Metals"; Biotechnology Advances; 23; pp. 97-114; (2005).

Sok, et al.; "Rsenite-lnducible RN-Associated Protein ( IR P) Protects Cells From Arsenite Toxicity"; Cell Stress & Chaperones; 6; pp. 6-15; (2001).

-& DATABSE UniProt [Online]; Mar. 1, 2002, "RecName: Full=Zinc finger AN1 and C2H2 domain-containing stress-associated protein 11; Short=AtSAP11;" Retrieved from EBI accession No. UNIPROT:Q8VZ42; Database accession No. Q8VZ42 the whole document.

International Search Report and Written Opinion; International Application No. PCT/US2008/064520; International Filing Date May 22, 2008; Date of Mailing Aug. 19, 2009; 18 pages.

Shubha et al.; "Genome-wide Analysis of the Stress Associated Protein (SAP) Gene Family Containing A20/AN1 Zinc-Finger(s) in Rice and Their Phylogenetic Relationship with *Arabidopsis*"; Mol Gen Genomics; 276; pp. 565-575; (2006).

International Preliminary Report on Patentability & Written Opinion; International Application No. PCT/US2008/064520; International Filing Date May 22, 2008; Date of Mailing Nov. 24, 2009; 9 pages.

Salt, et al.; "Phytoremediation: A Novel Strategy for the Removal of Toxic Metals from the Environment Using Plants"; Biotechnology; 13; pp. 468-474; (1995).

Guerinot, et al.; "Fortified Foods and Phytoremediation. Two Sides of the Same Coin"; Plant Physiology; 125; pp. 164-167; (2001).

\* cited by examiner

SEQUENCE LISTING

```
<160> NUMBER OF SEQ ID NOS: 34

<210> SEQ ID NO 1
<211> LENGTH: 840
<212> TYPE: DNA
<213> ORGANISM: Arabidopsis thaliana

<400> SEQUENCE: 1 atgggactc cggaatttcc agatctgggg aaacactgct ccgtcgatgt ttgcaagcaa      60
atcgatttct tgcctttcac ctgcgaccgt tgcctacagg tgttttgttt ggatcatcga    120
agctatatga acatagttg tccaaaaggc gatagagaag atgtgactgt agttatctgc    180
ccactctgtg ctaaaggagt ccgattaaac ccaaacgaag acccaaatat aacatgggag    240
aaacatgtca ataccgactg tgacccatca aactacgaaa aagctacaaa gaagaagaaa    300
tgtcccgttc caagatgcaa ggagtaccta actttctcca acaccatcaa gtgccgagat    360
tgcaatgtcg atcactgctt gaaacatcgt tttggacctg atcacacttg ccctggacca    420
agaaaactcc cattcatggg tttcttgagt agtagtacca ccagaaaaga agctaagaca    480
acaagaccca acaaagctca tccatcaact tcatcatctt cttcttcttc gagatggtct    540
aatctcctat cttcagcaga agcaggaatt agcaggctcg gtaatgacat tagccagaag    600
ctacagtttt cgagcagcaa agataatggt atcgtggagg tgtgtccaca gtgcggtgcg    660
aaattctctt cggttacttc tcttgtggaa catgtagaga aaacacatga gaggaacaag    720
aagcagaatc atggcaatgt cacggtcgat gtctgccta gatgtagcag aggattccgc    780
gatccagtag atcttgtgaa ccatatcgaa agagatcacc gaggcacttc gaaagcatag    840

<210> SEQ ID NO 2
<211> LENGTH: 750
<212> TYPE: DNA
<213> ORGANISM: Arabidopsis thaliana

<400> SEQUENCE: 2
atgggaactc cagaatttcc agatctgggt aaacactgct ccgtcgatta ttgcaaacag      60
atcgatttct tgcccttcac atgcgatcgc tgccttcagg tgtattgtct ggatcatcgt    120
agctatatga acacgattg tccaaaagga aacagaggag atgtcactgt ggttatttgt    180
ccattatgtg ctaaaggagt tagattaaac cctgacgaag atcccaacat cacctgggag    240
aaacatgtta atacagactg tgatccatct aactacgaaa aagctgtcaa gaagaagaaa    300
tgtcctgttc ctagatgcag agaactcttg acattctcca atactattaa atgtcgagat    360
tgtagcatcg atcattgttt gaaacatcgg tttggacctg atcatagttg ttctggaccc    420
aagaagcctg aatcgagttt ctcattcatg ggtttcttga gtacaaacac aaaagaagct    480
cctgcatcat catcatcttc ttcgagatgg tctagtcttt tcgcttctgc ggaagcaagt    540
attagtagac tcggtaacga tataagccag aagttacagt ttgcgagtgg caatgatggc    600
aattcagaga aaacgcaaga gaggaatgga aaacagaatt gtggcaaagt tacggttgat    660
```

```
gtttgtccca aatgtagtag agggtttcgt gatccggtgg atctattgaa gcatatcgat    720
aaggatcatc gtggcacttc taaagcctag                                     750
```

<210> SEQ ID NO 3
<211> LENGTH: 576
<212> TYPE: DNA
<213> ORGANISM: Arabidopsis thaliana

<400> SEQUENCE: 3

```
atggggactc cggaatttcc agatctaggg aaacactgct ccgtcgatgt tgcacgcag      60 atcgatttct tgcccttcac atgtgatcgc tgccttcagg tgctttgttt ggatcattgt    120
agctatatgt taaaccctga cgaagattca aacataactt gggataaaca tgttaatgat    180
acagattgtg atccctcaaa ctacgaaaac gatgttaaga agaagaagaa acaatgtcct    240
gtttctagtt gttctggacc gaaggaaccc gattcgagta tctcgagtac aaacacaaca    300
gtagctgcta caagcgctcc tgcatcatct tcatcttctt caatatcgtc tgctagtttt    360
ttcgcttcag ccgaagcacg ttttagaaag acaagattga atcggacaag attgaatcgg    420
gcaagattga atccgaccag ggaagatgaa atcctagag tggaaaacct ccctctatgg    480
atgatcaggg aaggagtggc tgatgtagta ggggaactga gacagat gagtcaggaa       540 gaagaagaag aagatgttga atgggaagaa gaataa                              576
```

<210> SEQ ID NO 4
<211> LENGTH: 561
<212> TYPE: DNA
<213> ORGANISM: Arabidopsis thaliana

<400> SEQUENCE: 4

```
atggcaggag gaggaacaga gcgtttcct gatcttggag agcattgcca agaccctgat      60
tgcaaattac tcgatttct cccttttact tgcgacggct gcaaattggt gttttgtttg    120
gagcatagat catacaagtc acataactgt ccgaaatccg atcatgggag cagaacggtt    180
tccatctgtg aaacatgttc aatagcgatt gaaacaactg gttttgatga aaaaggaatc    240
aaatctttgc ttgagaaaca cgaaagatcc ggagattgtg atccaaacaa gaaaagaaa     300 ccaacgtgtc ctgtaaaacg ttgcaaagag attctgactt tgcgaataa ccttacttgc     360 aaatattgtg gagtcaagtt ctgtttgaaa caccggtttc cgacagatca tgtctgtaac    420
aagaagatca ttaataccgc gggaacaagc tcgaggtgga acgagaggtt tatggaagct    480
ttgagtttaa gaaaccagaa agggtgtgga gagggagct ctgtttcatc aaaatcttca     540
ccatcagtta gatcgtttta g                                              561
```

<210> SEQ ID NO 5
<211> LENGTH: 393
<212> TYPE: DNA
<213> ORGANISM: Arabidopsis thaliana

<400> SEQUENCE: 5

```
atggtgaacg aaacagaagc attaccatgc gagggaggct gtggactcta cggcacccga     60
gtgaacaaca atctatgctc tctctgctac aaaaagagtg ttcttcaaca ctcgcccgct    120
ttaagattcg aacccgagac cgagcaatca cagtgttgcc ctcctacgaa tagtcccgcc    180
gttgaagaag aaccggtcaa aaaaggaga tgtgggatat gtaagaggaa ggtaggaatg     240
ttgggattca gtgtagatg tggacacatg ttttgcgggt cacatcgtta ccggaggag      300 cattcttgtc cctttgatta caaacaatct ggacggctcg ccttggccac acagttgcct    360
```

```
ttgatcagag ctgacaagtt gcagaggttt tag                          393
```

<210> SEQ ID NO 6
<211> LENGTH: 873
<212> TYPE: DNA
<213> ORGANISM: Oryza sativa

<400> SEQUENCE: 6

```
atggggacgc cggagttccc caacctgggc aagcactgca gcgtcggcga ctgcaaccag    60
atcgacttcc tgcccttcac ctgcgaccgc tgcgaccacg tcttttgcct tcagcaccga   120
agttatacat cgcatcagtg tccaaatgca aatcagaagg atgtgactgt cctcatctgc   180
ccactctgtg ctaaaggagt tcgcctgaac ccgaacgaag atccaaacat cacctgggac   240
acccatgtca atagtgactg tgatccatca aattaccaga agtaacaaa gaaaaagaaa    300
tgcccagtgc ctgggtgcag agagacactg acattttcaa acacaattag atgcaaagat   360
tgcaccaaag aacactgcct gaagcataga tttggacctg atcacaagtg tccagggcca   420
agaaaaccgg aatctacatt ccccttcgga aatatgctta ggagaagtca gaaagcagaa   480
tcatgttcaa attcaaacag cagtagcact agttcatcct ggtggagctc tagtcttctt   540
accgcagcaa cgagtttcaa atcatctgct gaagctggga tgcagaaatt gagcacagca   600
actacccaag ccatccagaa ggctaaggat gggatctcga caagcagcag taacagcggt   660
gatctcgtgg agcaatgtgt tcagtgccca gcaagatttt ccaccgtggg ggccttaatc   720
gagcattgcg aaaagtccca tcagagcaac tcgcaatcaa gtcgtagcag agtgacggtc   780
gatgtctgcc cgaaatgcag caaggcattt cgagatccag tgttgcttgt ggagcatgtt   840
gagagggacc atggaggaac gtcaagagcg tag                                873
```

<210> SEQ ID NO 7
<211> LENGTH: 567
<212> TYPE: DNA
<213> ORGANISM: Oryza sativa

<400> SEQUENCE: 7

```
atggcgcggc ggggcacgga ggcgttcccg gacctggggg cgcagtgcga cagggaggac    60
tgcaaccagc tcgacttcct ccccttcgac tgcgacggct gcggcaagac gttctgcgcg   120
gagcaccgga cgtaccggga ccacggctgc gcgcgcgccg cggaccaggg ccgcaccgtc   180
gtcgtctgcg aggcctgcgg cgacgccatc gagcggcggg ccggggacgg ggcgggggac   240
gacgccgccg tgctggaggc gcacgcgcgg tcgcggcggt gcgacccggc gaggaagcgc   300
aagccgcggt gccccgtgcc gcggtgcaag gagacgctca cgttctccaa cacgagcggg   360
tgcaaggggt gcggccagaa ggtgtgcctc aagcaccggt tccccgccga ccacgcgtgc   420
gccggcgcag gcgccggcgc ggcgtcgaag gccgccggcg ccgcggccgc cgcgaggagc   480
gccgggcagt gcgggcgcga cgcgcagaag aaggagggcg gcgggtggaa gctgccgcaa   540
tcggtgagga acatgaagat tttctga                                      567
```

<210> SEQ ID NO 8
<211> LENGTH: 279
<212> TYPE: PRT
<213> ORGANISM: Arabidopsis thaliana

<400> SEQUENCE: 8

```
Met Gly Thr Pro Glu Phe Pro Asp Leu Gly Lys His Cys Ser Val Asp
1               5                   10                  15

Val Cys Lys Gln Ile Asp Phe Leu Pro Phe Thr Cys Asp Arg Cys Leu
```

```
                    20                  25                  30
Gln Val Phe Cys Leu Asp His Arg Ser Tyr Met Lys His Ser Cys Pro
            35                  40                  45

Lys Gly Asp Arg Glu Asp Val Thr Val Val Ile Cys Pro Leu Cys Ala
        50                  55                  60

Lys Gly Val Arg Leu Asn Pro Asn Glu Asp Pro Asn Ile Thr Trp Glu
65                  70                  75                  80

Lys His Val Asn Thr Asp Cys Asp Pro Ser Asn Tyr Glu Lys Ala Thr
                85                  90                  95

Lys Lys Lys Lys Cys Pro Val Pro Arg Cys Lys Glu Tyr Leu Thr Phe
            100                 105                 110

Ser Asn Thr Ile Lys Cys Arg Asp Cys Asn Val Asp His Cys Leu Lys
        115                 120                 125

His Arg Phe Gly Pro Asp His Thr Cys Pro Gly Pro Arg Lys Leu Pro
        130                 135                 140

Phe Met Gly Phe Leu Ser Ser Thr Thr Arg Lys Glu Ala Lys Thr
145                 150                 155                 160

Thr Arg Pro Asn Lys Ala His Pro Ser Thr Ser Ser Ser Ser Ser Ser
                165                 170                 175

Ser Arg Trp Ser Asn Leu Leu Ser Ser Ala Glu Ala Gly Ile Ser Arg
            180                 185                 190

Leu Gly Asn Asp Ile Ser Gln Lys Leu Gln Phe Ser Ser Ser Lys Asp
        195                 200                 205

Asn Gly Ile Val Glu Val Cys Pro Gln Cys Gly Ala Lys Phe Ser Ser
        210                 215                 220

Val Thr Ser Leu Val Glu His Val Glu Lys Thr His Glu Arg Asn Lys
225                 230                 235                 240

Lys Gln Asn His Gly Asn Val Thr Val Asp Val Cys Pro Arg Cys Ser
                245                 250                 255

Arg Gly Phe Arg Asp Pro Val Asp Leu Val Asn His Ile Glu Arg Asp
            260                 265                 270

His Arg Gly Thr Ser Lys Ala
        275

<210> SEQ ID NO 9
<211> LENGTH: 249
<212> TYPE: PRT
<213> ORGANISM: Arabidopsis thaliana

<400> SEQUENCE: 9

Met Gly Thr Pro Glu Phe Pro Asp Leu Gly Lys His Cys Ser Val Asp
1               5                   10                  15

Tyr Cys Lys Gln Ile Asp Phe Leu Pro Phe Thr Cys Asp Arg Cys Leu
            20                  25                  30

Gln Val Tyr Cys Leu Asp His Arg Ser Tyr Met Lys His Asp Cys Pro
            35                  40                  45

Lys Gly Asn Arg Gly Asp Val Thr Val Val Ile Cys Pro Leu Cys Ala
        50                  55                  60

Lys Gly Val Arg Leu Asn Pro Asp Glu Asp Pro Asn Ile Thr Trp Glu
65                  70                  75                  80

Lys His Val Asn Thr Asp Cys Asp Pro Ser Asn Tyr Glu Lys Ala Val
                85                  90                  95

Lys Lys Lys Lys Cys Pro Val Pro Arg Cys Arg Glu Leu Leu Thr Phe
            100                 105                 110

Ser Asn Thr Ile Lys Cys Arg Asp Cys Ser Ile Asp His Cys Leu Lys
```

```
                    115                 120                 125
His Arg Phe Gly Pro Asp His Ser Cys Ser Gly Pro Lys Lys Pro Glu
130                 135                 140

Ser Ser Phe Ser Phe Met Gly Phe Leu Ser Thr Asn Thr Lys Glu Ala
145                 150                 155                 160

Pro Ala Ser Ser Ser Ser Ser Arg Trp Ser Ser Leu Phe Ala Ser
                    165                 170                 175

Ala Glu Ala Ser Ile Ser Arg Leu Gly Asn Asp Ile Ser Gln Lys Leu
                180                 185                 190

Gln Phe Ala Ser Gly Asn Asp Gly Asn Ser Glu Lys Thr Gln Glu Arg
            195                 200                 205

Asn Gly Lys Gln Asn Cys Gly Lys Val Thr Val Asp Val Cys Pro Lys
        210                 215                 220

Cys Ser Arg Gly Phe Arg Asp Pro Val Asp Leu Leu Lys His Ile Asp
225                 230                 235                 240

Lys Asp His Arg Gly Thr Ser Lys Ala
                245

<210> SEQ ID NO 10
<211> LENGTH: 191
<212> TYPE: PRT
<213> ORGANISM: Arabidopsis thaliana

<400> SEQUENCE: 10

Met Gly Thr Pro Glu Phe Pro Asp Leu Gly Lys His Cys Ser Val Asp
1               5                   10                  15

Val Cys Thr Gln Ile Asp Phe Leu Pro Phe Thr Cys Asp Arg Cys Leu
                20                  25                  30

Gln Val Leu Cys Leu Asp His Cys Ser Tyr Met Leu Asn Pro Asp Glu
            35                  40                  45

Asp Ser Asn Ile Thr Trp Asp Lys His Val Asn Asp Thr Asp Cys Asp
        50                  55                  60

Pro Ser Asn Tyr Glu Asn Asp Val Lys Lys Lys Lys Gln Cys Pro
65                  70                  75                  80

Val Ser Ser Cys Ser Gly Pro Lys Glu Pro Asp Ser Ser Ile Ser Ser
                85                  90                  95

Thr Asn Thr Thr Val Ala Ala Thr Ser Ala Pro Ala Ser Ser Ser Ser
                100                 105                 110

Ser Ser Ile Ser Ser Ala Ser Phe Phe Ala Ser Ala Glu Ala Arg Phe
            115                 120                 125

Arg Lys Thr Arg Leu Asn Arg Thr Arg Leu Asn Arg Ala Arg Leu Asn
        130                 135                 140

Pro Thr Arg Glu Asp Glu Asp Pro Arg Val Glu Asn Leu Pro Leu Trp
145                 150                 155                 160

Met Ile Arg Glu Gly Val Ala Asp Val Val Gly Glu Leu Arg Gly Gln
                165                 170                 175

Met Ser Gln Glu Glu Glu Glu Glu Asp Val Glu Trp Glu Glu Glu
            180                 185                 190

<210> SEQ ID NO 11
<211> LENGTH: 186
<212> TYPE: PRT
<213> ORGANISM: Arabidopsis thaliana

<400> SEQUENCE: 11

Met Ala Gly Gly Gly Thr Glu Ala Phe Pro Asp Leu Gly Glu His Cys
1               5                   10                  15
```

```
Gln Asp Pro Asp Cys Lys Leu Leu Asp Phe Leu Pro Phe Thr Cys Asp
             20                  25                  30

Gly Cys Lys Leu Val Phe Cys Leu Glu His Arg Ser Tyr Lys Ser His
         35                  40                  45

Asn Cys Pro Lys Ser Asp His Gly Ser Arg Thr Val Ser Ile Cys Glu
     50                  55                  60

Thr Cys Ser Ile Ala Ile Glu Thr Thr Gly Phe Asp Glu Lys Gly Ile
 65                  70                  75                  80

Lys Ser Leu Leu Glu Lys His Glu Arg Ser Gly Asp Cys Asp Pro Asn
                 85                  90                  95

Lys Lys Lys Lys Pro Thr Cys Pro Val Lys Arg Cys Lys Glu Ile Leu
            100                 105                 110

Thr Phe Ala Asn Asn Leu Thr Cys Lys Tyr Cys Gly Val Lys Phe Cys
        115                 120                 125

Leu Lys His Arg Phe Pro Thr Asp His Val Cys Asn Lys Lys Ile Ile
    130                 135                 140

Asn Thr Ala Gly Thr Ser Ser Arg Trp Asn Glu Arg Phe Met Glu Ala
145                 150                 155                 160

Leu Ser Leu Arg Asn Gln Lys Gly Cys Gly Arg Gly Ser Ser Val Ser
                165                 170                 175

Ser Lys Ser Ser Pro Ser Val Arg Ser Phe
            180                 185

<210> SEQ ID NO 12
<211> LENGTH: 130
<212> TYPE: PRT
<213> ORGANISM: Arabidopsis thaliana

<400> SEQUENCE: 12

Met Val Asn Glu Thr Glu Ala Leu Pro Cys Glu Gly Gly Cys Gly Leu
 1               5                  10                  15

Tyr Gly Thr Arg Val Asn Asn Asn Leu Cys Ser Leu Cys Tyr Lys Lys
             20                  25                  30

Ser Val Leu Gln His Ser Pro Ala Leu Arg Phe Glu Pro Glu Thr Glu
         35                  40                  45

Gln Ser Gln Cys Cys Pro Pro Thr Asn Ser Pro Ala Val Glu Glu Glu
     50                  55                  60

Pro Val Lys Lys Arg Arg Cys Gly Ile Cys Lys Arg Lys Val Gly Met
 65                  70                  75                  80

Leu Gly Phe Lys Cys Arg Cys Gly His Met Phe Cys Gly Ser His Arg
                 85                  90                  95

Tyr Pro Glu Glu His Ser Cys Pro Phe Asp Tyr Lys Gln Ser Gly Arg
            100                 105                 110

Leu Ala Leu Ala Thr Gln Leu Pro Leu Ile Arg Ala Asp Lys Leu Gln
        115                 120                 125

Arg Phe
    130

<210> SEQ ID NO 13
<211> LENGTH: 290
<212> TYPE: PRT
<213> ORGANISM: Oryza sativa

<400> SEQUENCE: 13

Met Gly Thr Pro Glu Phe Pro Asn Leu Gly Lys His Cys Ser Val Gly
 1               5                  10                  15
```

```
Asp Cys Asn Gln Ile Asp Phe Leu Pro Phe Thr Cys Asp Arg Cys Asp
             20                  25                  30

His Val Phe Cys Leu Gln His Arg Ser Tyr Thr Ser His Gln Cys Pro
         35                  40                  45

Asn Ala Asn Gln Lys Asp Val Thr Val Leu Ile Cys Pro Leu Cys Ala
 50                  55                  60

Lys Gly Val Arg Leu Asn Pro Asn Glu Asp Pro Asn Ile Thr Trp Asp
 65                  70                  75                  80

Thr His Val Asn Ser Asp Cys Asp Pro Ser Asn Tyr Gln Lys Val Thr
                 85                  90                  95

Lys Lys Lys Lys Cys Pro Val Pro Gly Cys Arg Glu Thr Leu Thr Phe
             100                 105                 110

Ser Asn Thr Ile Arg Cys Lys Asp Cys Thr Lys Glu His Cys Leu Lys
             115                 120                 125

His Arg Phe Gly Pro Asp His Lys Cys Pro Gly Pro Arg Lys Pro Glu
         130                 135                 140

Ser Thr Phe Pro Phe Gly Asn Met Leu Arg Arg Ser Gln Lys Ala Glu
145                 150                 155                 160

Ser Cys Ser Asn Ser Asn Ser Ser Thr Ser Ser Ser Trp Trp Ser
                 165                 170                 175

Ser Ser Leu Leu Thr Ala Ala Thr Ser Phe Lys Ser Ser Ala Glu Ala
             180                 185                 190

Gly Met Gln Lys Leu Ser Thr Ala Thr Thr Gln Ala Ile Gln Lys Ala
         195                 200                 205

Lys Asp Gly Ile Ser Thr Ser Ser Asn Ser Gly Asp Leu Val Glu
210                 215                 220

Gln Cys Val Gln Cys Pro Ala Arg Phe Ser Thr Val Gly Ala Leu Ile
225                 230                 235                 240

Glu His Cys Glu Lys Ser His Gln Ser Asn Ser Gln Ser Ser Arg Ser
                 245                 250                 255

Arg Val Thr Val Asp Val Cys Pro Lys Cys Ser Lys Ala Phe Arg Asp
             260                 265                 270

Pro Val Leu Leu Val Glu His Val Glu Arg Asp His Gly Gly Thr Ser
         275                 280                 285

Arg Ala
 290

<210> SEQ ID NO 14
<211> LENGTH: 188
<212> TYPE: PRT
<213> ORGANISM: Oryza sativa

<400> SEQUENCE: 14

Met Ala Arg Arg Gly Thr Glu Ala Phe Pro Asp Leu Gly Ala Gln Cys
1               5                  10                  15

Asp Arg Glu Asp Cys Asn Gln Leu Asp Phe Leu Pro Asp Cys Asp
             20                  25                  30

Gly Cys Gly Lys Thr Phe Cys Ala Glu His Arg Thr Tyr Arg Asp His
         35                  40                  45

Gly Cys Ala Arg Ala Ala Asp Gln Gly Arg Thr Val Val Cys Glu
 50                  55                  60

Ala Cys Gly Asp Ala Ile Glu Arg Arg Ala Gly Asp Gly Gly Asp
 65                  70                  75                  80

Asp Ala Ala Val Leu Glu Ala His Ala Arg Ser Arg Arg Cys Asp Pro
             85                  90                  95
```

```
Ala Arg Lys Arg Lys Pro Arg Cys Pro Val Pro Arg Cys Lys Glu Thr
            100                 105                 110

Leu Thr Phe Ser Asn Thr Ser Gly Cys Lys Gly Cys Gly Gln Lys Val
        115                 120                 125

Cys Leu Lys His Arg Phe Pro Ala Asp His Ala Cys Ala Gly Ala Gly
        130                 135                 140

Ala Gly Ala Ala Ser Lys Ala Ala Gly Ala Ala Ala Ala Ala Arg Ser
145                 150                 155                 160

Ala Gly Gln Cys Gly Arg Asp Ala Gln Lys Lys Glu Gly Gly Gly Trp
                165                 170                 175

Lys Leu Pro Gln Ser Val Arg Asn Met Lys Ile Phe
            180                 185
```

<210> SEQ ID NO 15
<211> LENGTH: 1395
<212> TYPE: DNA
<213> ORGANISM: Arabidopsis thaliana

<400> SEQUENCE: 15

```
aagcttgcat gctgatctca aatacattga tacatatctc atctagatct aggttatcat    60
tatgtaagaa agttttgacg aatatggcac gacaaaatgg ctagactcga tgtaattggt   120
atctcaactc aacattatac ttataccaaa cattagttag acaaaattta acaactatt    180
ttttatgtat gcaagagtca gcatatgtat aattgattca gaatcgtttt gacgagttcg   240
gatgtagtag tagccattat ttaatgtaca tactaatcgt gaatagtgaa tatgatgaaa   300
cattgtatct tattgtataa atatccataa acacatcatg aaagacactt tctttcacgg   360
tctgaattaa ttatgataca attctaatag aaaacgaatt aaattacgtt gaattgtatg   420
aaatctaatt gaacaagcca accacgacga cgactaacgt tgcctggatt gactcggttt   480
aagttaacca ctaaaaaaac ggagctgtca tgtaacacgc ggatcgagca ggtcacagtc   540
atgaagccat caaagcaaaa gaactaatcc aagggctgag atgattaatt agtttaaaaa   600
ttagttaaca cgagggaaaa ggctgtctga cagccaggtc acgttatctt tacctgtggt   660
cgaaatgatt cgtgtctgtc gatttttaatt attttttttga aaggccgaaa ataaagttgt   720
aagagataaa cccgcctata taaattcata tattttcctc tccgctttga attgtctcgt   780
tgtcctcctc actttcatca gccgttttga atctccggcg acttgacaga agaacaag    840
gaagaagact aagagagaaa gtaagagata tccaggaga ttcattctcc gttttgaatc    900
ttcctcaatc tcatcttctt ccgctctttc tttccaaggt aataggaact ttctggatct   960
actttatttg ctggatctcg atcttgtttt ctcaatttcc ttgagatctg gaattcgttt  1020
aatttggatc tgtgaacctc cactaaatct tttggtttta ctagaatcga tctaagttga  1080
ccgatcagtt agctcgatta tagctaccag aatttggctt gaccttgatg gagagatcca  1140
tgttcatgtt acctgggaaa tgatttgtat atgtgaattg aaatctgaac tgttgaagtt  1200
agattgaatc tgaacactgt caatgttaga ttgaatctga acactgttta aggttagatg  1260
aagtttgtgt atagattctt cgaaacttta ggatttgtag tgtcgtacgt tgaacagaaa  1320
gctatttctg attcaatcag ggtttatttg actgtattga actcttttg tgtgtttgca   1380
gctcataaac catgg                                                    1395
```

<210> SEQ ID NO 16
<211> LENGTH: 1266
<212> TYPE: DNA
<213> ORGANISM: Oryza sativa

<400> SEQUENCE: 16

```
tagctagcat actcgaggtc attcatatgc ttgagaagag agtcgggata gtccaaaata    60
aaacaaaggt aagattacct ggtcaaaagt gaaaacatca gttaaaaggt ggtataagta   120
aaatatcggt aataaaaggt ggcccaaagt gaaatttact cttttctact attataaaaa   180
ttgaggatgt tttgtcggta ctttgatacg tcattttttgt atgaattggt ttttaagttt   240
attcgcgatt tggaaatgca tatctgtatt tgagtcggtt tttaagttcg ttgcttttgt   300
aaatacagag ggatttgtat aagaaatatc tttaaaaaac ccatatgcta atttgacata   360
attttttgaga aaaatatata ttcaggcgaa ttccacaatg aacaataata agattaaaat   420
agcttgcccc cgttgcagcg atgggtattt tttctagtaa aataaaagat aaacttagac   480
tcaaaacatt tacaaaaaca ccccctaaag tcctaaagcc caaagtgcta tgcacgatcc   540
atagcaagcc cagcccaacc caacccaacc caacccaccc cagtgcagcc aactggcaaa   600
tagtctccac ccccggcact atcaccgtga gttgtccgca ccaccgcacg tctcgcagcc   660
aaaaaaaaaa aagaaagaa aaaaagaaa agaaaaaca gcaggtgggt ccgggtcgtg    720
ggggccggaa aagcgaggag gatcgcgagc agcgacgagg cccggccctc cctccgcttc   780
caaagaaacg ccccccatcg ccactatata catacccccc cctctcctcc catcccccca   840
accctaccac caccaccacc accacctcct ccccccctcgc tgccggacga cgagctcctc   900
cccccctcccc ctccgccgcc gccggtaacc accccgcccc tctcctcttt ctttctccgt   960
ttttttttc gtctcggtct cgatctttgg ccttggtagt ttgggtgggc gagagcggct  1020
tcgtcgccca gatcggtgcg cgggaggggc gggatctcgc ggctggcgtc tccgggcgtg  1080
agtcggcccg gatcctcgcg gggaatgggg ctctcggatg tagatcttct ttctttcttc  1140
tttttgtggt agaatttgaa tccctcagca ttgttcatcg gtagttttc ttttcatgat  1200
ttgtgacaaa tgcagcctcg tgcggagctt ttttgtaggt agaagatggc tgacgccgag  1260
gatatc                                                            1266
```

<210> SEQ ID NO 17
<211> LENGTH: 1871
<212> TYPE: DNA
<213> ORGANISM: Glycine max

<400> SEQUENCE: 17

```
gagctccacc gcggtggcgg ccgctctaga gcgcgtcgac tcacattctt gcccgcctga    60
tgaatgctca tccggaattc agtggaagtg gtgcagaaga ggggagggaa tgtttggggt   120
acatgatttg aaaaaagggg agaatgatta gaagagatag aaaattggca gaccaacatt   180
gaaggattca taggaatgtt gtgtgctagt aaattggaca aatgttgctc ttgatatttt   240
cagcatatca ttcatcttag aagcccaact gttctttttt atatatattc tctgttgcct   300
tcctttcctt caaacacgg cttttgaatt ttgaaccatt aactgagttg gaatagtggt   360
aaaatcatgt agattttcct tttcgttttg tggggatatg aatacgaaat atccttacaa   420
ccagacaaag ctgtggctca gaagaaagag aaacatgcct cactgctaga atcactagaa   480
ctcacatctt gtatacaaac tgttatacca aactgagaat tttacaattt ccaaagatgc   540
aattctcaac cattaaccaa tttcatctta aacactaaca gttcctcagt cttgaacttt   600
ccatgctgaa aatttgttgc ctatttcttt tataggcagt ggcttcttat gagagtcaca   660
ctctctgaac ttcttacgta atacttgact tttcattttg tgctttataa ttgttatctc   720
atgcattgca cttttaagat aaggttgttg tgcattgttt ggttgagtgc aacgatttac   780
```

-continued

```
tgattaccat agctacttgt ggatcttata ttttcaaaag tgtatgcttg gtcattaatc       840
aaccaagcat gataagcccc atcatctacc accccttcta taccatatac gcattttgct       900
tatctacatt gctactgtta cactcaaaca agtctaacag ataatacgtt aagttaatga       960
acatttttag taatattatt ataaggattg gccaatgtaa ttgtgaagag agaagcatgc      1020
tttaagctac ccaacaaaat ggataagagt ttcagttgat atggttctct tgtttctttt      1080
ccaataaaaa accaacttta aaatataaaa tttactgtaa caaggaaca aagagttttc       1140
acttaatcca tgaatgagaa aggatggtca caaaatatgt taggttaata tggaatgagg      1200
gcactgtgca aactacacaa ataatatcaa ttccaccacc atcacacatt tacgttcttc      1260
caaggaagag ataagataat ggagcctcca cgtgtcacct ccacatggta cctaacaata      1320
aggctaccat tcaaaatttt cctcactcgt gtggcctata tgctgtaatg tcatcactta      1380
ttcaatccaa cggttgtaac ttttcggcaa ccaatcctct ccatttcaca ccattggatt      1440
agtactacac aaatcacact attatatata gcaagtttga gcagaagcta ggatatctgg      1500
cagcagaaaa acaagtagtt ggatcctaag aagaagaaac catggcccgg aagcttgtc       1560
atttgaaaat ttgcaaagca tctgtagcca ccccactttg tttgttgtac ttaaactaca      1620
ttcccatttg tttttgcttt atgagatttc atcatcctgt attttggtt tctgttttcg       1680
gacttcaatg gaaattaatg gatgagaact aatgaataag ctattgtgtt gtgttgcttt      1740
gtttccaaat aacttcaaga acccattgtc cttgcatttc catcttgtgg gttgaaatta      1800
gtctcttcta aatttaagtt aattgtgtca ctaaatgatg gttaacaaag ctcgaggggg      1860
gccccggtacc c                                                          1871
```

<210> SEQ ID NO 18
<211> LENGTH: 2098
<212> TYPE: DNA
<213> ORGANISM: Escherichia coli

<400> SEQUENCE: 18

```
gttaactaac gttatccttg ggcgtttctt tccattgcgt aaaacatcgc gctggcaaga        60
gaaagctacc ggctggctga aacgctatgg tgcagtcacg ctattattaa gctggatgcc       120
cgtggttggc gatttactgt gtctgttagc gggatggatg cgcatctcgt ggggaccggt       180
aatctttttt ttgtgccttg gtaaagcgtt acgctatgtt gcagttgcag cagcgaccgt       240
tcagggcatg atgtggtggc actaattgta ggcctgcaca tatggtcacc attacagtta       300
tgctaattaa aacgattttg acaggcggga ggtcaattttg atcccggacg tatcacaggc       360
gctggcctgg ctggaaaaac atcctcaggc gttaaagggg atacagcgtg gctggagcg       420
cgaaactttg cgtgttaatg ctgatggcac actggcaaca acaggtcatc ctgaagcatt       480
aggttccgca ctgacgcaca aatggattac taccgatttt gcggaagcat tgctggaatt       540
cattacacca gtggatggtg atattgaaca tatgctgacc tttatgcgcg atctgcatcg       600
ttatacggcg cgcaatatgg gcgatgagcg gatgttgccg ttaagtatgc catgctacat       660
cgcagaaggt caggacatcg aactggcaca gtacggcact tctaacaccg gacgctttaa       720
aacgctgtat cgtgaagggc tgaaaaatcg ctacggcgcg ctgatgcaaa ccatttccgg       780
cgtgcactac aatttctctt tgccaatggc attctggcaa gcgaagtgcg gtgatatctc       840
gggcgctgat gccaaagaga aaatttctgc gggctatttc gcgttatcc gcaattacta       900
tcgtttcggt tgggtcattc cttatctgtt tggtgcatct ccggcgattt gttcttcttt       960
cctgcaagga aaaccaacgt cgctgccgtt tgagaaaacc gagtgcggta tgtattaccct     1020
```

```
gccgtatgcg acctctcttc gtttgagcga tctcggctat accaataaat cgcaaagcaa    1080
tcttggtatt accttcaacg atctttacga atacgtagcg ggccttaaac aggcaatcaa    1140
aacgccatcg gaagagtacg cgaagattgg tattgagaaa gacggtaaga ggctgcaaat    1200
caacagcaac gtgttgcaga ttgaaaacga actgtacgcg ccgattcgtc aaaacgcgt     1260
tacccgcagc ggcgagtcgc cttctgatgc gctgttacgt ggcggcattg aatatattga    1320
agtgcgttcg ctggacatca acccgttctc gccgattggt gtagatgaac agcaggtgcg    1380
attcctcgac ctgtttatgg tctggtgtgc gctggctgat gcaccggaaa tgagcagtag    1440
cgaacttgcc tgtacacgcg ttaactggaa ccgggtgatc ctcgaaggtc gcaaaccggg    1500
tctgacgctg ggtatcggct gcgaaaccgc acagttcccg ttaccgcagg tgggtaaaga    1560
tctgttccgc gatctgaaac gcgtcgcgca aacgctggat agtattaacg gcggcgaagc    1620
gtatcagaaa gtgtgtgatg aactggttgc ctgcttcgat aatcccgatc tgactttctc    1680
tgcccgtatc ttaaggtcta tgattgatac tggtattggc ggaacaggca agcatttgc     1740
agaagcctac cgtaatctgc tgcgtgaaga gccgctggaa attctgcgcg aagaggattt    1800
tgtagccgag cgcgagggct tcgaacgccg tcagcaggaa atggaagccg ctgataccga    1860
accgtttgcg gtgtggctgg aaaaacacgc ctgacagaaa agaaaaaggc cactcgtgag    1920
tggccaaaat ttcatctctg aattcaggga tgatgataac aaatgcgcgt ctttcatata    1980
ctcagactcg cctgggaaga aagagttcag aaaattttta aaaaattac cggaggtggc     2040
taaatgccgt tgttagatag cttcacagtc gatcataccc ggatggaagc gcctgcag      2098

<210> SEQ ID NO 19
<211> LENGTH: 951
<212> TYPE: DNA
<213> ORGANISM: Escherichia coli

<400> SEQUENCE: 19
atgatcaagc tcggcatcgt gatggacccc atcgcaaaca tcaacatcaa gaaagattcc     60
agttttgcta tgttgctgga agcacagcgt cgtggttacg aacttcacta tatggagatg    120
ggcgatctgt atctgatcaa tggtgaagcc cgcgcccata cccgcacgct gaacgtgaag    180
cagaactacg aagagtggtt ttcgttcgtc ggtgaacagg atctgccgct ggccgatctc    240
gatgtgatcc tgatgcgtaa agacccgccg tttgataccg agtttatcta cgcgacctat    300
attctggaac gtgccgaaga gaaagggacg ctgatcgtta acaagccgca gagcctgcgc    360
gactgtaacg agaaactgtt taccgcctgg ttctctgact aacgccagaa acgctggtt    420
acgcgcaata agcgcagctc aaaagcgttc tgggagaaac acagcgacat cattcttaag    480
ccgctggacg gtatgggcgg cgcgtcgatt ttccgcgtga agaaggcga tccaaacctc    540
ggcgtgattg ccgaaaccct gactgagcat ggcactcgct actgcatggc gcaaaattac    600
ctgccagcca ttaaagatgg cgacaaacgc gtgctggtgg tggatggcga gccggtaccg    660
tactgcctgg cgcgtattcc gcaggggggc gaaacccgtg gcaatctggc tgccggtggt    720
cgcggtgaac tcgtccgct gacggaaagt gactggaaaa tcgcccgtca gatcgggccg    780
acgctgaaag aaaaagggct gattttttgtt ggtctggata tcatcggcga ccgtctgact    840
gaaattaacg tcaccagccc aacctgtatt cgtgagattg aagcagagtt ccggtgtcg     900
atcaccggaa tgttaatgga tgccatcgaa gcacgtttac agcagcagta a              951

<210> SEQ ID NO 20
<211> LENGTH: 1245
<212> TYPE: DNA
```

<213> ORGANISM: Schizosaccharomyces pombe

<400> SEQUENCE: 20

```
atgaacattg ttaaacgagc agtcccagaa ttactgagag gaatgaccaa tgcaacacca      60
aatatcggtt tgattaaaaa caaggtagta agctttgaag ctgtcggaca actcaaaaaa     120
tcttttaca  aaagacaatt gcctaaacaa tgtttagctt ttgattcatc tctcggtaaa     180
gatgttttt  tacgagcatt gcaagaggga cggatggaaa attatttttc gcttgcacag     240
cagatggtaa cccaaaacga accagctttt tgtggattgg gaactctctg catgattctt     300
aattcgctta aagttgaccc gggtagatta tggaagggat cttggcgctg gtatgatcag     360
tatatgcttg attgttgtcg atcgctaagc gatattgaaa aagatggtgt tacgctagaa     420
gagttctctt gtttagctaa ctgcaatggc cttcggacta ttacgaaatg tgtcaaagat     480
gttagctttg atgaatttcg gaaagacgta atctcttgtt ctaccattga gaataaaatt     540
atggcaattt cattttgccg gaaagtgctc ggtcaaacag gcgatggaca tttttagtcca    600
gttggaggct tcagtgaaag tgataacaag atattaatat tggacgttgc tcgatttaaa    660
tatccttgct actgggtgga tttgaagctc atgtacgaga gtatgtttcc tatcgataaa    720
gctagcggcc aacctagagg ctatgtactt ttagagccaa tgcatattcc tttaggtgtg    780
cttacagtcg gtttaaacaa gtacagctgg cgaaacgttt ccaagcatat actgcagcag    840
gcggcaacgg taaaaaacgc agacaatttg gctgaaatac ttttatccat taatcaatca    900
tcaattcctc taatccaaga acgctccaac agttcaaagt ctggtgattt cgagcatttt    960
aaagaatgta ttagaagcac aaaaacatat catttatttc tgaaacatac gaataccaat    1020
gttgaatata tcactatggc tttttgggct atattttcct tacccatgat ccaaaaagcg    1080
cttcccaaag gcgttctaga agagattcaa tctttattga aagaagttga aatttccgaa    1140
attaacactc aactaactgc gttgaaaaaa cagcttgata gtttaaccca ttgttgtaaa    1200
actgacactg ggtgttgtag ttcaagctgc tgtaaaaata cgtga                    1245
```

<210> SEQ ID NO 21
<211> LENGTH: 40
<212> TYPE: DNA
<213> ORGANISM: Artificial Sequence
<220> FEATURE:
<223> OTHER INFORMATION: Primer

<400> SEQUENCE: 21

```
tacgtcgaat tcaggaggta gaccatgggg actccggaat                            40
```

<210> SEQ ID NO 22
<211> LENGTH: 37
<212> TYPE: DNA
<213> ORGANISM: Artificial Sequence
<220> FEATURE:
<223> OTHER INFORMATION: Primer

<400> SEQUENCE: 22

```
tagctggtcg acaagcttct atgctttcga agtgcct                               37
```

<210> SEQ ID NO 23
<211> LENGTH: 47
<212> TYPE: DNA
<213> ORGANISM: Artificial Sequence
<220> FEATURE:
<223> OTHER INFORMATION: Primer

<400> SEQUENCE: 23

```
tacgtcggat ccaggaggta gaccatggga actccagaat ttccaga          47
```

<210> SEQ ID NO 24
<211> LENGTH: 40
<212> TYPE: DNA
<213> ORGANISM: Artificial Sequence
<220> FEATURE:
<223> OTHER INFORMATION: Primer

<400> SEQUENCE: 24

```
tagctgctcg agaagcttct aggctttaga agtgccacga                  40
```

<210> SEQ ID NO 25
<211> LENGTH: 40
<212> TYPE: DNA
<213> ORGANISM: Artificial Sequence
<220> FEATURE:
<223> OTHER INFORMATION: Primer

<400> SEQUENCE: 25

```
tacgtcgaat tcaggaggta gaccatgggg actccggaat                  40
```

<210> SEQ ID NO 26
<211> LENGTH: 41
<212> TYPE: DNA
<213> ORGANISM: Artificial Sequence
<220> FEATURE:
<223> OTHER INFORMATION: Primer

<400> SEQUENCE: 26

```
tagctggtcg acaagctttt attcttcttc ccattcaaca t                41
```

<210> SEQ ID NO 27
<211> LENGTH: 49
<212> TYPE: DNA
<213> ORGANISM: Artificial Sequence
<220> FEATURE:
<223> OTHER INFORMATION: Primer

<400> SEQUENCE: 27

```
tacgtcggat ccaggaggta gaccatggca ggaggaggaa cagaagcgt        49
```

<210> SEQ ID NO 28
<211> LENGTH: 34
<212> TYPE: DNA
<213> ORGANISM: Artificial Sequence
<220> FEATURE:
<223> OTHER INFORMATION: Primer

<400> SEQUENCE: 28

```
tagctggaat tcctaaaacg atctaactga tggt                        34
```

<210> SEQ ID NO 29
<211> LENGTH: 46
<212> TYPE: DNA
<213> ORGANISM: Artificial Sequence
<220> FEATURE:
<223> OTHER INFORMATION: Primer

<400> SEQUENCE: 29

```
tacgtcggat ccaggaggta gaccatggtg aacgaaacag aagcat           46
```

<210> SEQ ID NO 30
<211> LENGTH: 40
<212> TYPE: DNA
<213> ORGANISM: Artificial Sequence
<220> FEATURE:

```
<223> OTHER INFORMATION: Primer

<400> SEQUENCE: 30
tagctgctcg agaagcttct aaaacctctg caacttgtca                    40

<210> SEQ ID NO 31
<211> LENGTH: 49
<212> TYPE: DNA
<213> ORGANISM: Artificial Sequence
<220> FEATURE:
<223> OTHER INFORMATION: Primer

<400> SEQUENCE: 31
tacgtcggat ccggactaaa ggaggccatg gggacgccgg agttcccca          49

<210> SEQ ID NO 32
<211> LENGTH: 44
<212> TYPE: DNA
<213> ORGANISM: Artificial Sequence
<220> FEATURE:
<223> OTHER INFORMATION: Primer

<400> SEQUENCE: 32
tagctgctcg agctacgctc ttgacgttcc tccgtggtcc ctct               44

<210> SEQ ID NO 33
<211> LENGTH: 47
<212> TYPE: DNA
<213> ORGANISM: Artificial Sequence
<220> FEATURE:
<223> OTHER INFORMATION: Primer

<400> SEQUENCE: 33
tacgtcggat ccggactaaa ggaggccatg gcgcggcggg gcacgga            47

<210> SEQ ID NO 34
<211> LENGTH: 31
<212> TYPE: DNA
<213> ORGANISM: Artificial Sequence
<220> FEATURE:
<223> OTHER INFORMATION: Primer

<400> SEQUENCE: 34
tagctgctcg agtcagaaaa tcttcatgtt t                             31
```

METAL RESISTANT PLANTS AND METHODS OF MANUFACTURE THEREOF

CROSS-REFERENCE TO RELATED APPLICATIONS

This application is a continuation of U.S. Nonprovisional application Ser. No. 12/125,362, filed May 22, 2008, which claims priority to U.S. Provisional Patent Application Ser. No. 60/939,751, filed May 23, 2007, all of which are incorporated by reference herein in its entirety.

BACKGROUND

Abiotic stresses such as drought, salt, nutrient deficiency, and exposure to toxic metals adversely affect the growth and productivity of crop plants and thus are serious threats to global agricultural production and food security. These environmental stresses reduces crop yield by more than 30 to 50%, which not only cause the loss of billions of dollars annually, but also threaten the sustainability of the global agricultural industry.

Metal and metalloid pollutants such as arsenic (As), cadmium (Cd), chromium (Cr), lead (Pb), mercury (Hg), and zinc (Zn), can adversely affect the health of millions of people worldwide. Arsenic, for example, is toxic and carcinogenic. The metal and metalloid contaminated soil, sediment, and water supplies are major sources of contamination in the food chain. Metal and metalloid poisoning can occur via ingestion of contaminated drinking water and food. Industrial pollution and agricultural practices including the use of metal and metalloid-containing pesticides, herbicides, fertilizers, and wood preservatives, as well as irrigation with contaminated groundwater, and mining have significantly increased metal and metalloid contamination in agricultural soil. There is global concern regarding arsenic contamination in drinking water and soil, particularly on the Indian subcontinent where more than 450 million people are at risk for arsenic poisoning.

There are many different ways metal and metalloid pollutants can enter the food chain. Plants grown in contaminated soil can accumulate high levels of metal and metalloid pollutants in roots, shoots, and grain. Metal and metalloid pollutant uptake by plants may play an important role in the introduction of these pollutants into the food chain, for example, by the direct ingestion of contaminated grain. In addition, contaminated straw that is used as cattle feed may have adverse health effects on cattle and may result in increased metal and metalloid exposure in humans via a plant-animal-human pathway. There is, therefore, concern regarding the accumulation of metal and metalloid pollutants in meat and dairy products as well as in agricultural crops and vegetables.

In addition, metal and metalloid pollutants are phytotoxic and cause significant loss in crop yields. For example, arsenate is a phosphate analog and competes with phosphate for uptake in plants causing the inhibition of phosphate and other nutrients. Thus, arsenic contamination is an agricultural concern. A plant that is resistant to metal and metalloid pollutants and can accumulate a large biomass despite the presence of metal and metalloid pollutants will be advantageous as a biofuel plant. Such a plant could be grown on contaminated, but otherwise arable, land.

Metals and metalloids are often present in the environment in different ionic forms. With respect to arsenic, the arsenate oxyanions, $HAsO_4^{2-}$ and $H_2AsO_4^-$, are the most prevalent forms of arsenic in surface soil, water, and within cells, and these oxyanions contain arsenic in the pentavalent state [As(V)]. Arsenite, which at neutral pH contains arsenic in the trivalent oxidation state [As(III)] and likely as the acid $HAsO_3^{2-}$, is highly reactive and readily forms As(III)-thiol complexes. Plants use arsenate reductases to detoxify arsenic by reducing As(V) to As(III), which is subsequently detoxified via forming complexes with thiol-reactive peptides such as γ-glutamylcysteine (γ-EC), glutathione (GSH) and phytochelatins (PCs). It is suggested that these As(III)-thiol complexes are then sequestered into vacuoles by glutathione-conjugating pumps. It is further believed that plants trap arsenite in below ground tissues in order to prevent access to above ground reproductive tissues to prevent possible mutagenic consequences.

Similarly, another environmental factors, such as salinity, heat, cold, drought, and floods can limit the amount of arable land for crop production as well as reduce crop yields. Developing crops with enhanced abiotic stress tolerance will undoubtedly have an important effect on global food production and will help to alleviate an increasingly imminent threat of famine.

Accordingly, there is a need to develop novel plants that are resistant to environmental or abiotic stresses.

SUMMARY

Disclosed herein is a transgenic plant transformed with an isolated nucleic acid comprising a plant arsenite-inducible RNA-associated protein coding sequence operatively linked to a plant-expressible transcription regulatory sequence, wherein the plant arsenite-inducible RNA-associated protein (AIRAP) coding sequence encodes a polypeptide that is at least 95% identical to a polypeptide sequence of SEQ ID NO:8, SEQ ID NO:9, SEQ ID NO:10, SEQ ID NO:11, SEQ ID NO:12, SEQ ID NO:13, or SEQ ID NO:14, wherein the plant arsenite-inducible RNA-associated protein coding sequence encodes a polypeptide that confers resistance to an environmental stress, wherein greater than or equal to about 25% of transgenic plants are resistant to an environmental stress, and wherein the environmental stress inhibits the growth of wild type plants.

Further disclosed is a method for producing a transgenic plant that is resistant to an environmental stress comprising introducing an isolated nucleic acid comprising an plant arsenite-inducible RNA-associated protein coding sequence that encodes a polypeptide that is at least 95% identical to a polypeptide sequence selected from the group consisting of SEQ ID NO:8, SEQ ID NO:9, SEQ ID NO:10, SEQ ID NO:11, SEQ ID NO:12, SEQ ID NO:13, and SEQ ID NO:14 operatively linked to a plant-expressible transcription regulatory sequence into a plant cell or plant tissue; producing a transgenic plant cell or tissue comprising the isolated nucleic acid; and regenerating the transgenic plant cell or transgenic plant tissue to provide a transgenic plant that is resistant to an environmental stress, wherein greater than or equal to about 25% of transgenic plants are resistant to the environmental stress, and wherein the environmental stress inhibits the growth of wild type plants.

BRIEF DESCRIPTION OF THE DRAWINGS

FIG. 1 shows a sequence alignment of the following plant SAP proteins: AtAIRAP1 (new name AtSAP11) (SEQ ID NO:8); AtAIRAP2 (new name AtSAP13) (SEQ ID NO:9); AtAIRAP3 (new name AtSAP14) (SEQ ID NO:10); AtAIRAP4 (new name AtSAP12) (SEQ ID NO:11); AtAIRAP5 (new name AtSAP10) (SEQ ID NO:12);

Figure 2:
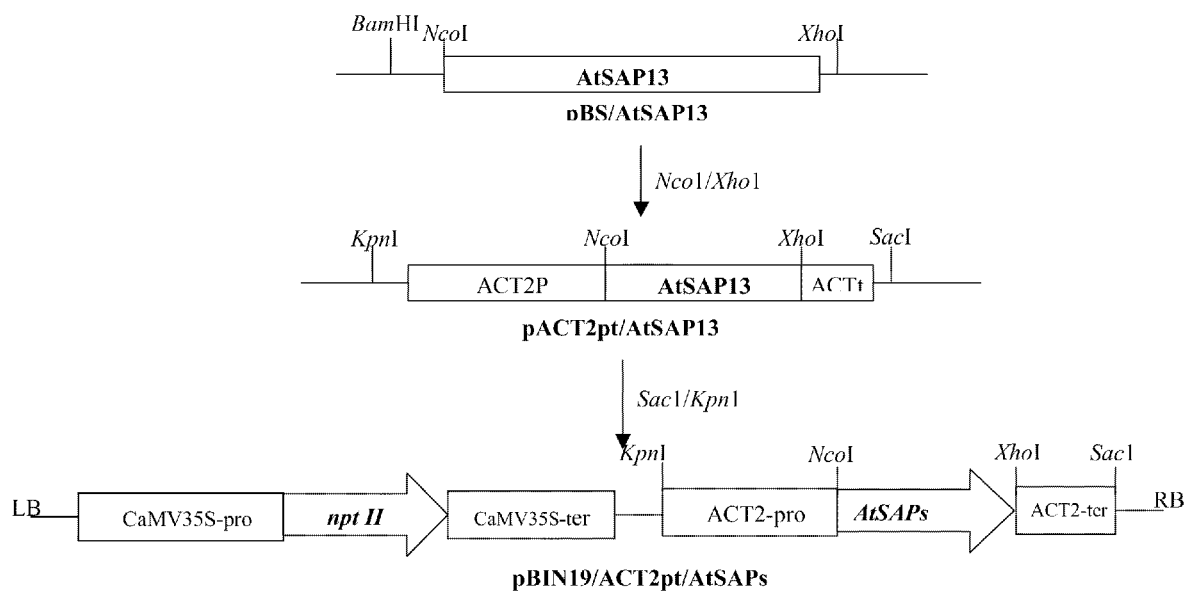
Figure 3:
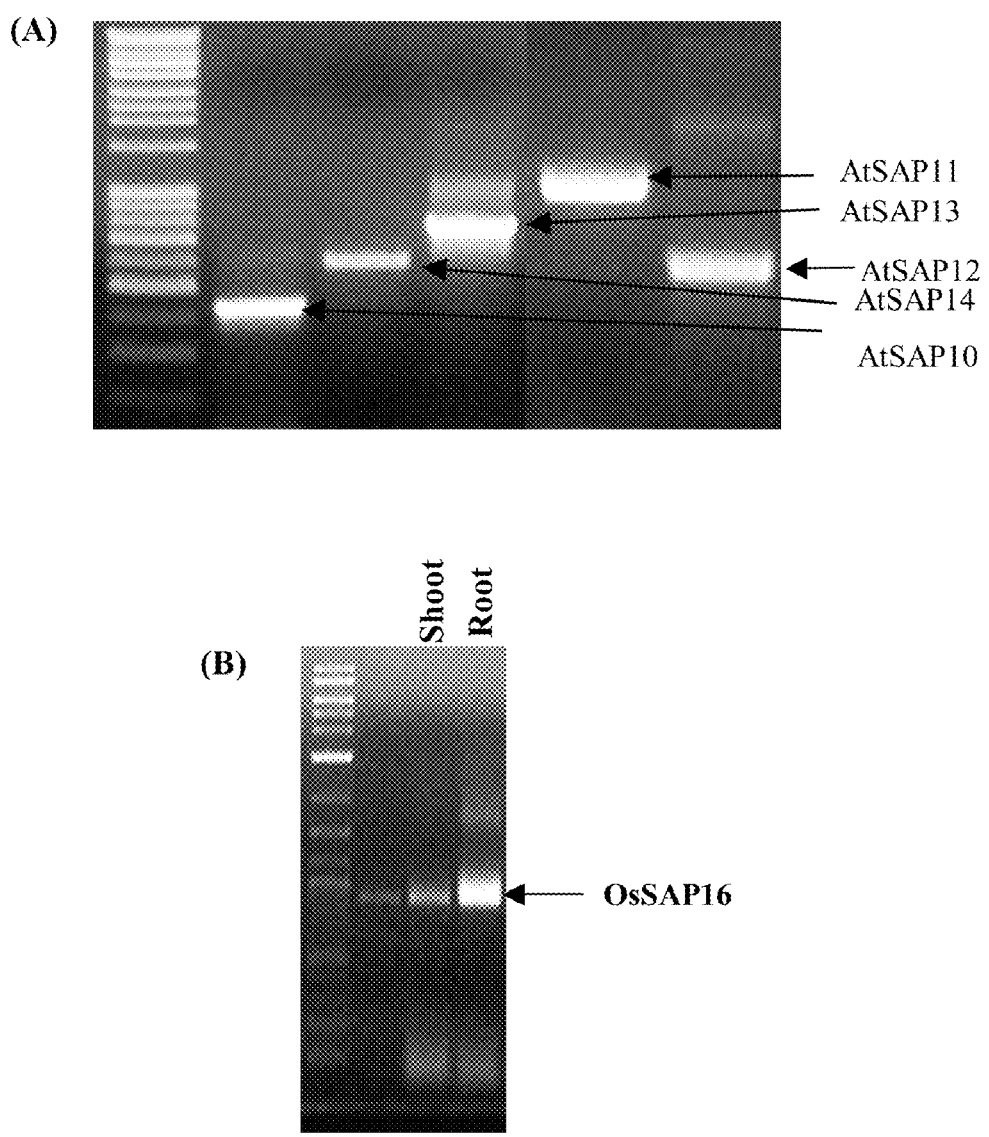
Figure 4:
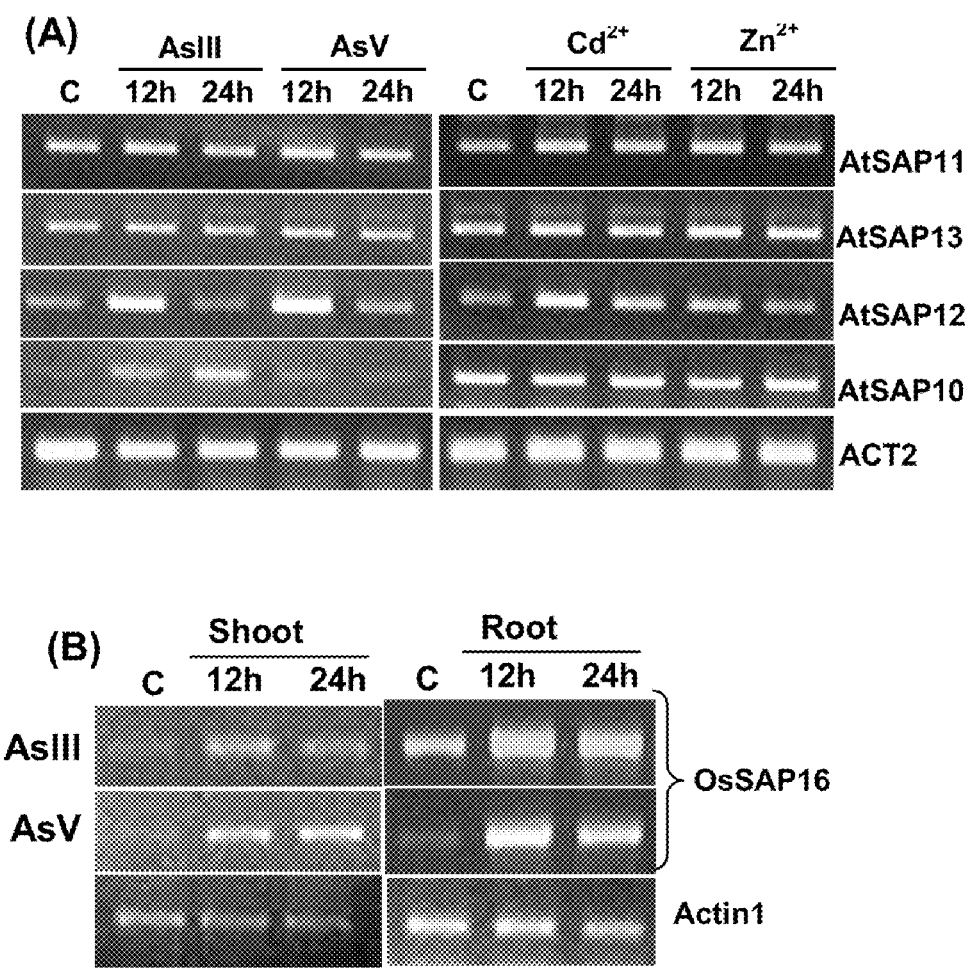
Figure 5:
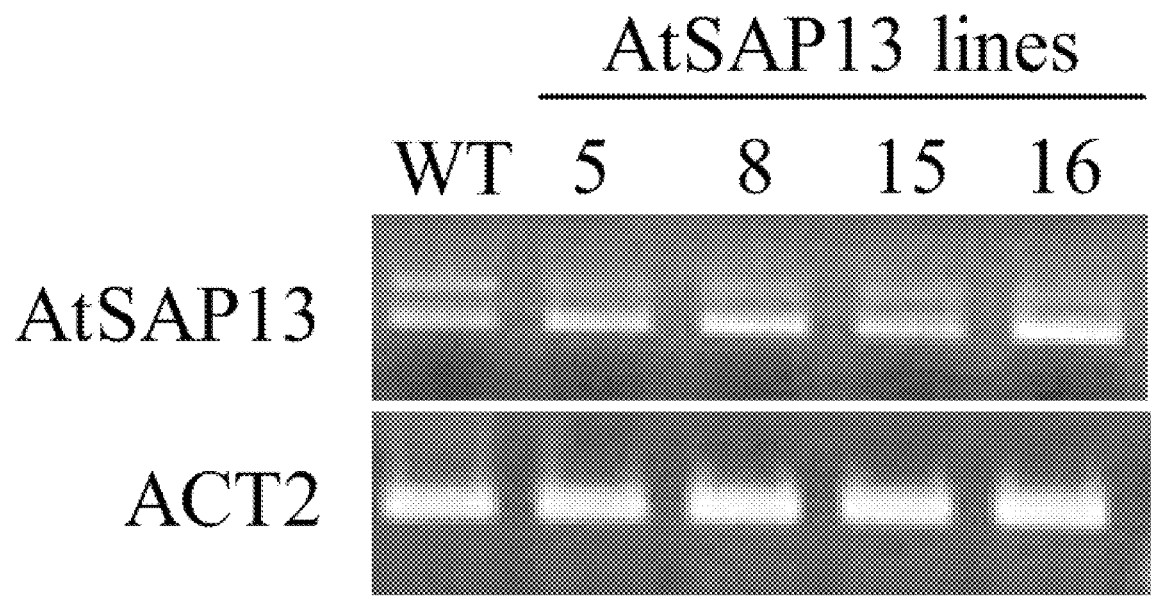
Figure 6:
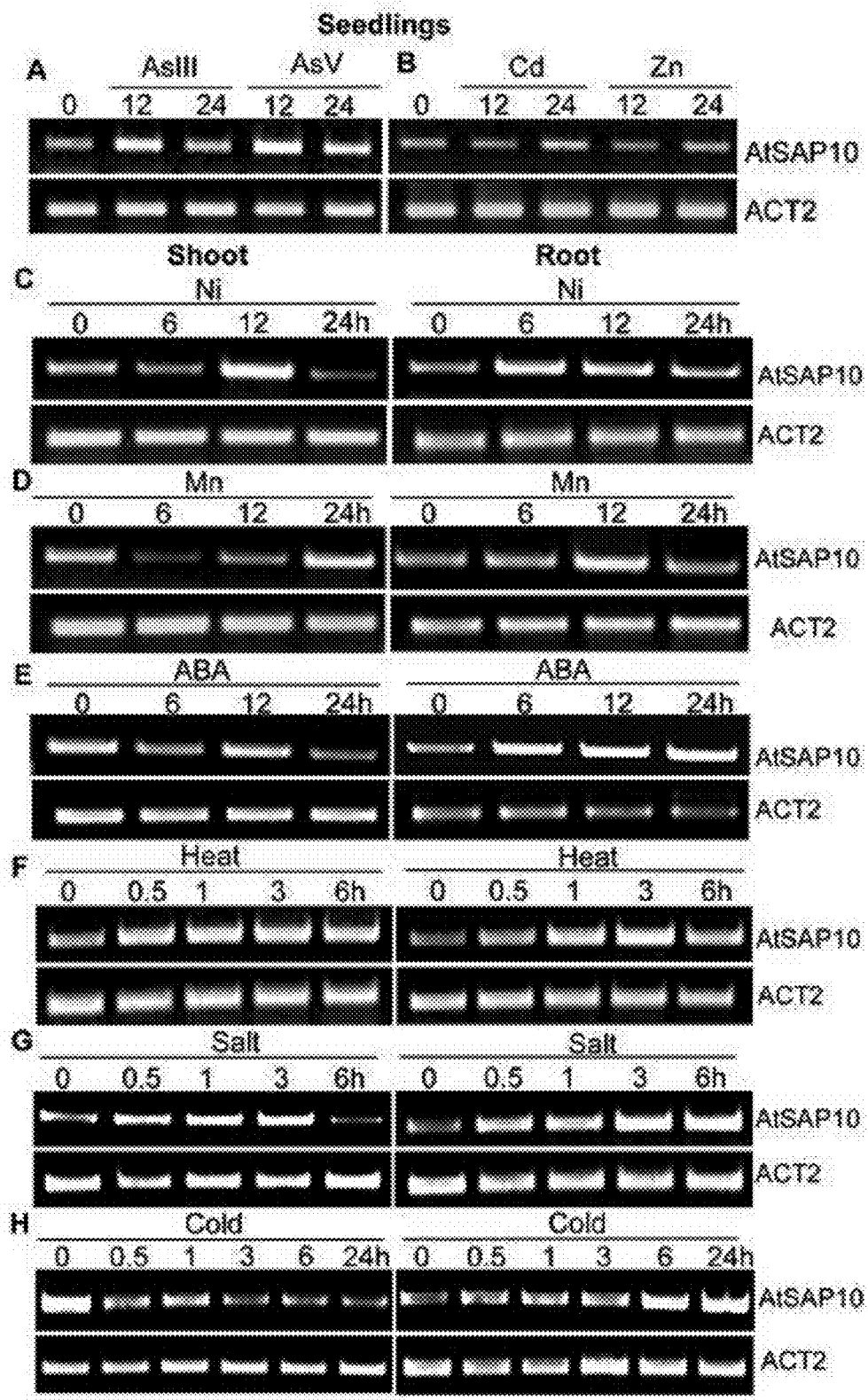
Figure 7:
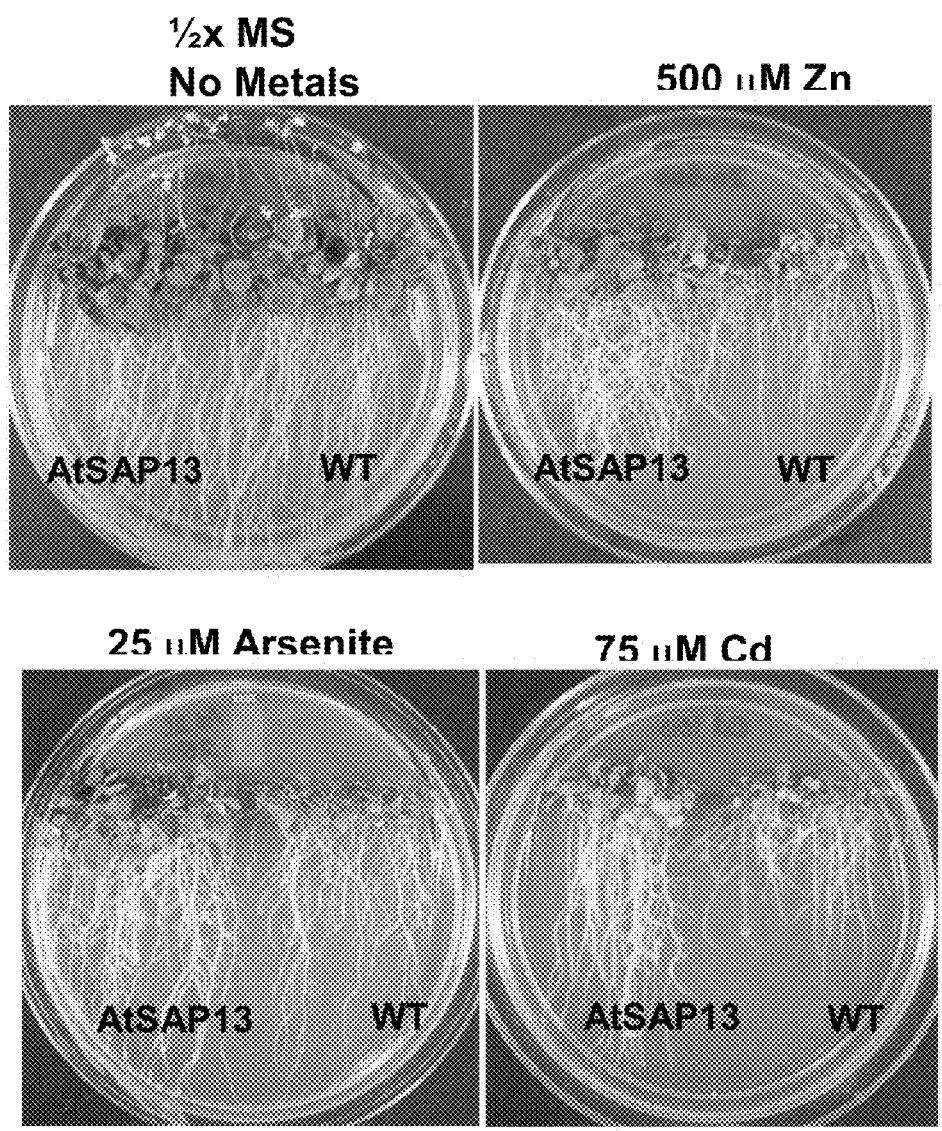
Figure 8:
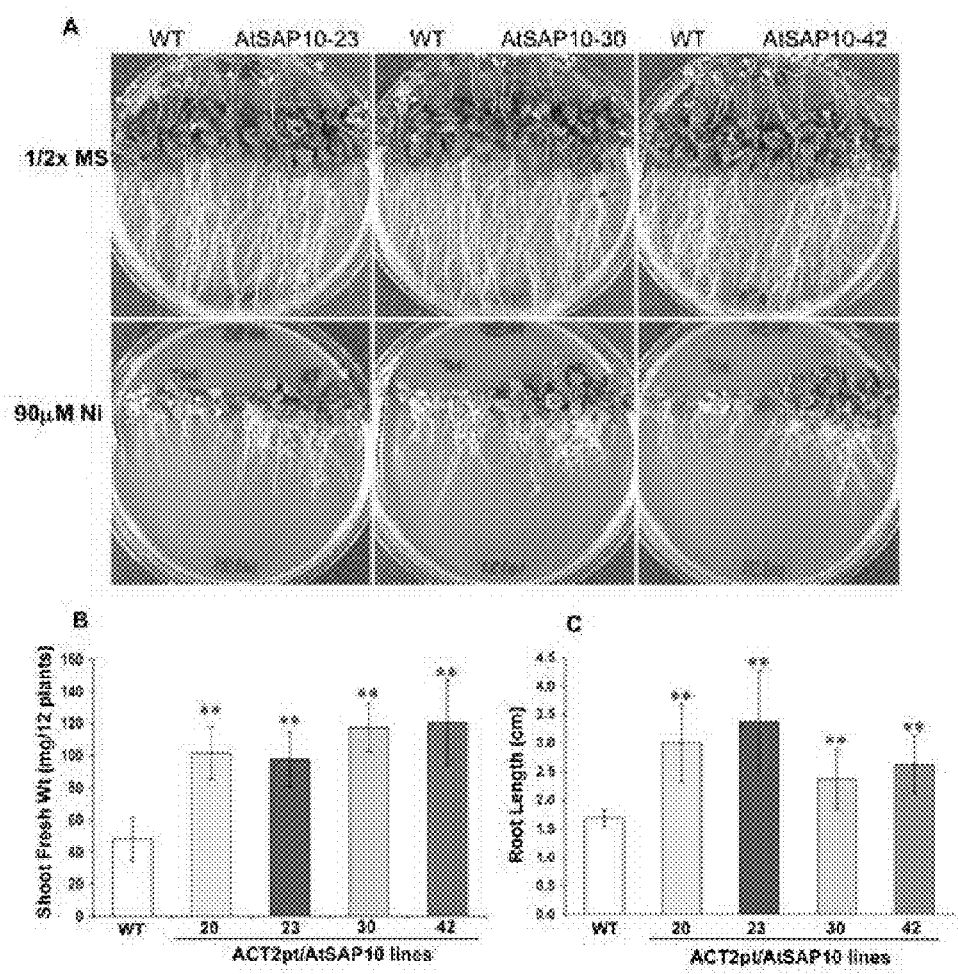
Figure 9:
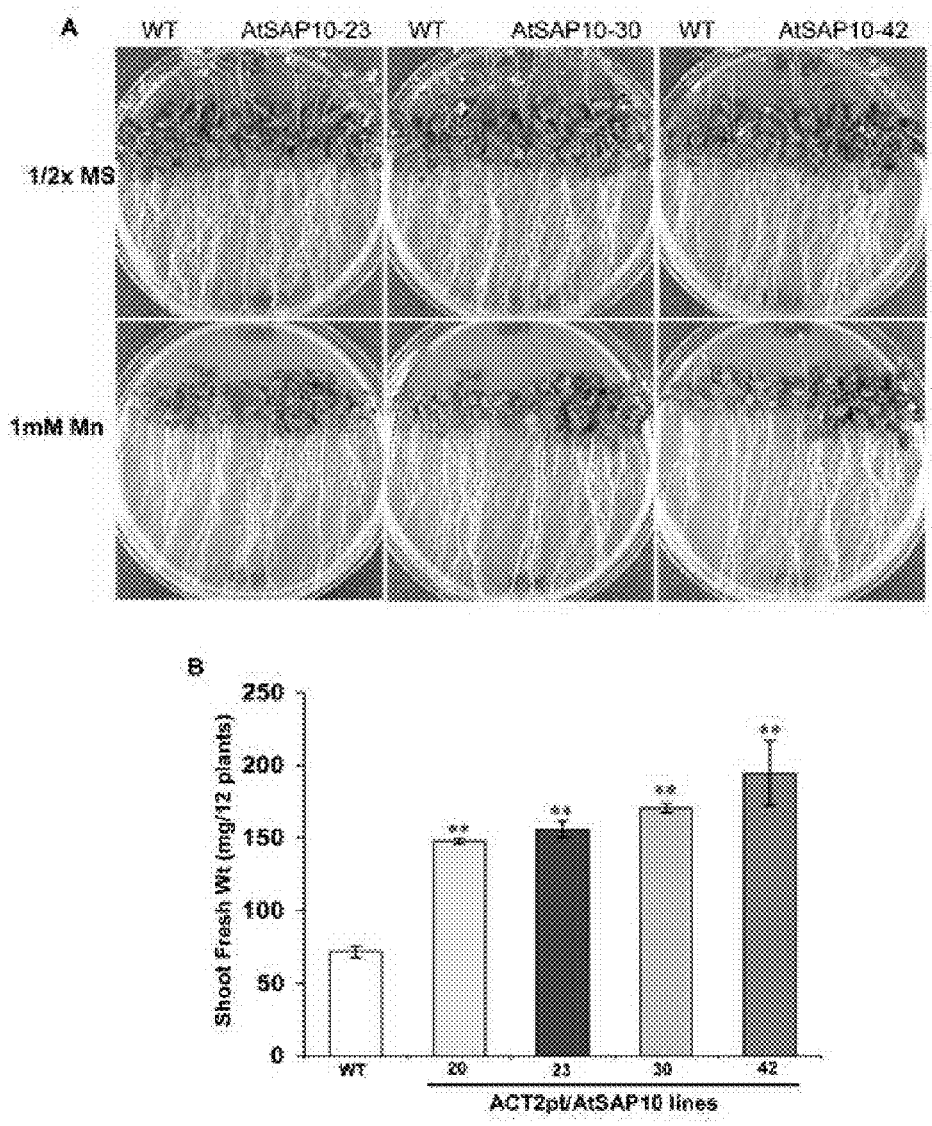
Figure 10:
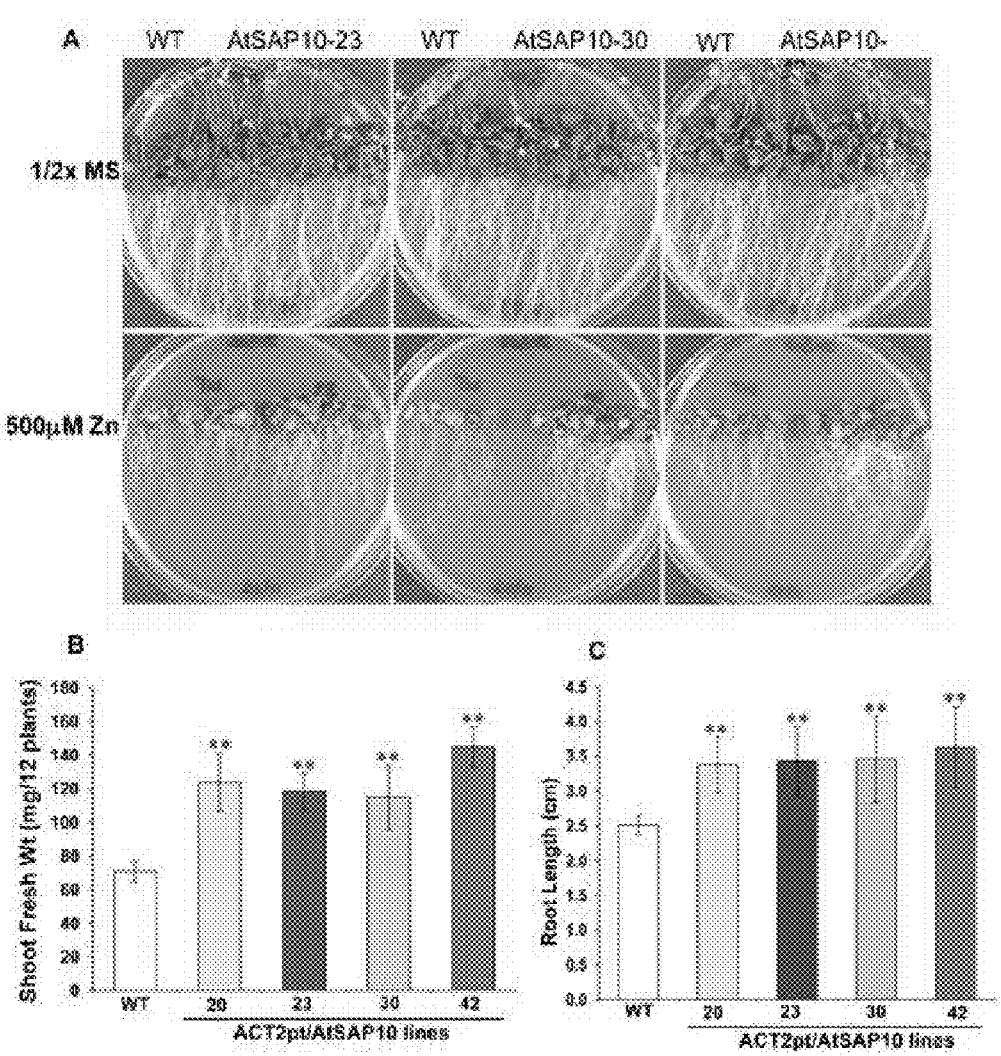
Figure 11:
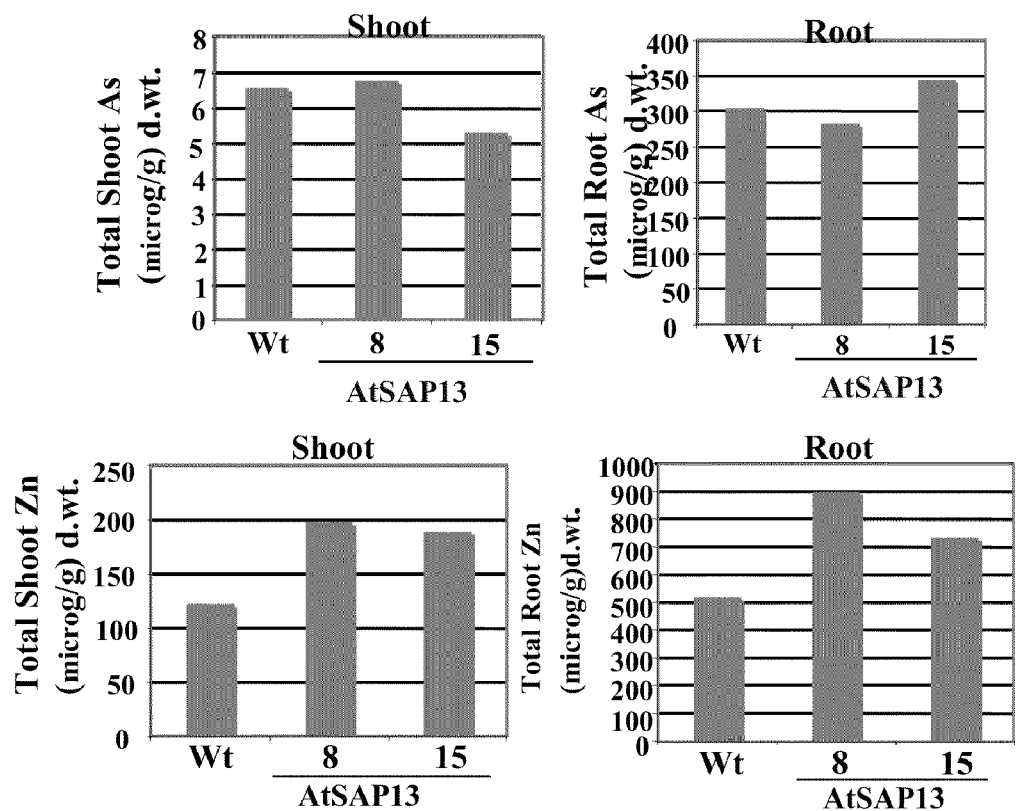
Figure 12:
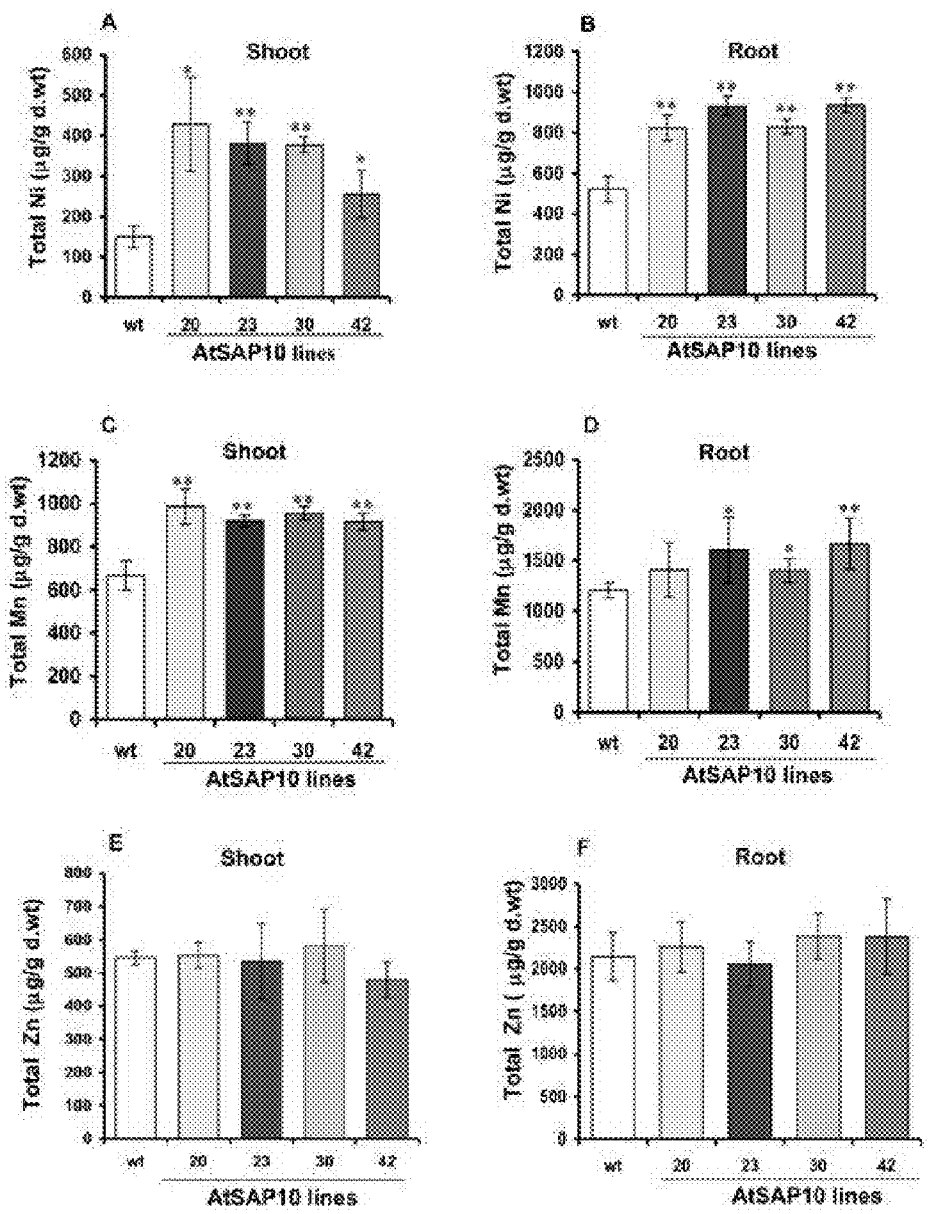
Figure 13:
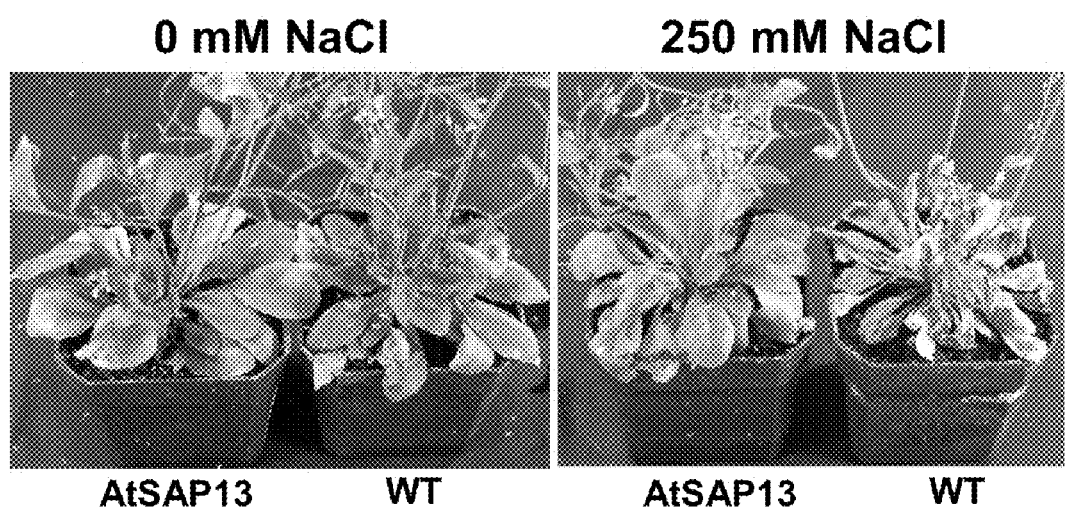
Figure 14:
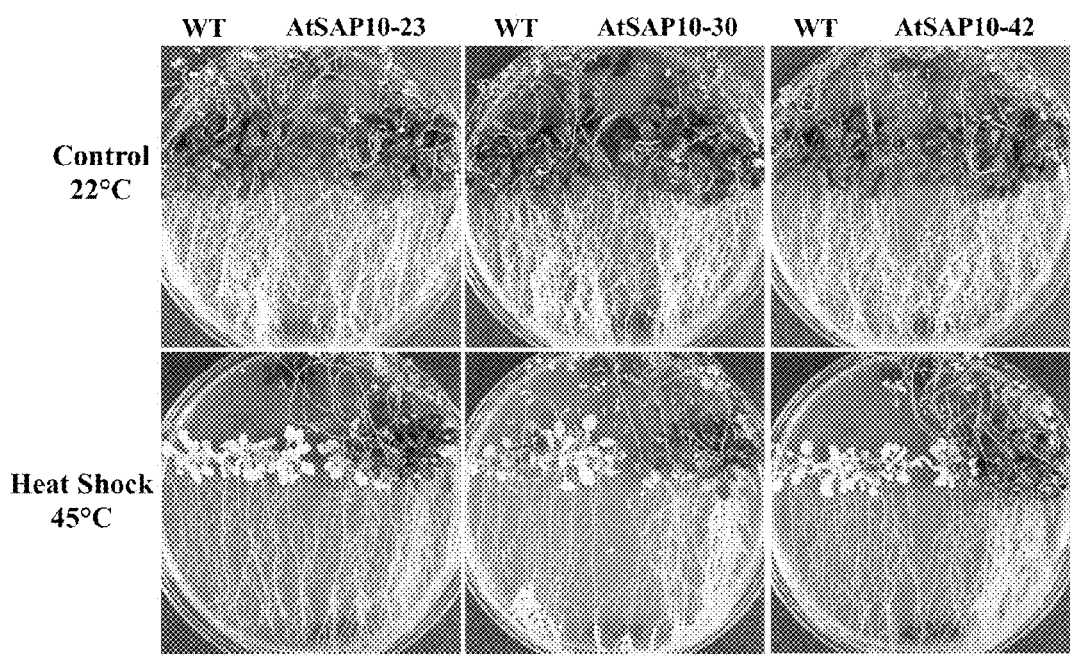

OsAIRAP1 (new name OsSAP16) (SEQ ID NO:13); and OsAIRAP2 (new name OsSAP17) (SEQ ID NO:14);

FIG. 2 shows a schematic diagram of a cloning strategy of a representative vector construct used to transform plants;

FIG. 3 shows PCR amplification of *Arabidopsis* and rice SAP cDNAs;

FIG. 4 shows PCR amplification of *Arabidopsis* and rice SAP cDNAs after metal or metalloid induction;

FIG. 5 shows PCR amplification of AtSAP13 cDNA from several transgenic *Arabidopsis* lines;

FIG. 6 shows semi-quantitative RT-PCR analysis of AtSAP10 expression in response to various stress treatments;

FIG. 7 shows a transgenic *Arabidopsis* line that is resistant to several metals and metalloids;

FIG. 8 shows a transgenic *Arabidopsis* line that is resistant to nickel;

FIG. 9 shows a transgenic *Arabidopsis* line that is resistant to manganese;

FIG. 10 shows a transgenic *Arabidopsis* line that is resistant to zinc;

FIG. 11 shows metal and metalloid accumulation in a transgenic *Arabidopsis* line;

FIG. 12 shows metal and metalloid accumulation in a transgenic *Arabidopsis* line;

FIG. 13 shows salt resistance in a transgenic *Arabidopsis* line;

FIG. 14 shows heat resistance in a transgenic *Arabidopsis* line; and

Figure 15:
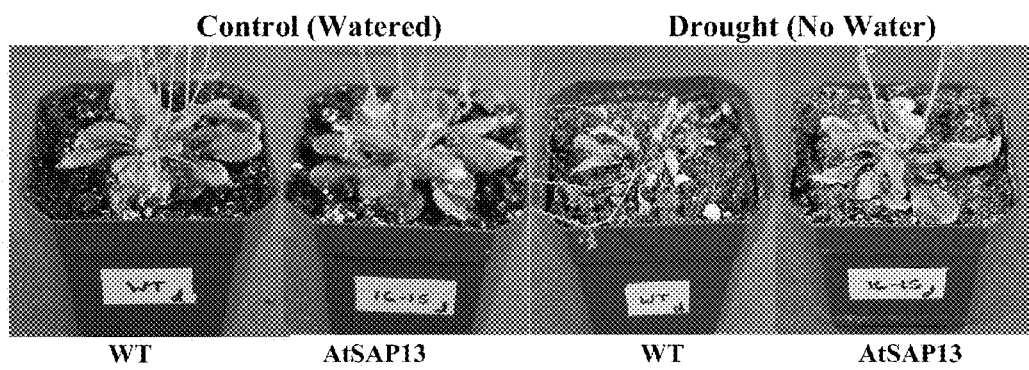

FIG. 15 shows drought resistance in a transgenic *Arabidopsis* line.

DETAILED DESCRIPTION

Disclosed herein is an isolated nucleic acid comprising a sequence at least 95% identical to the nucleotide sequence of AtSAP11 (GenBank No. At2g41835; SEQ ID NO:1); AtSAP13 (GenBank No. At3g57480; SEQ ID NO:2); AtSAP14 (GenBank No. At5g48205; SEQ ID NO:3); AtSAP12 (GenBank No. At3g28210; SEQ ID NO:4); AtSAP10 (GenBank No. At4g25380; SEQ ID NO:5); OsSAP16 (GenBank No. Os09g38240.1; SEQ ID NO:6); or OsSAP17 (GenBank No. Os09g21710.1; SEQ ID NO:7). In another embodiment, the isolated nucleic acid encodes a polypeptide that confers resistance to an environmental stress when expressed in a plant.

Disclosed herein also is an isolated nucleic acid comprising a sequence that encodes a polypeptide that is at least 95% identical to the amino acid sequence of AtSAP11 (GenBank No. At2g41835; SEQ ID NO:8); AtSAP13 (GenBank No. At3g57480; SEQ ID NO:9); AtSAP14 (GenBank No. At5g48205; SEQ ID NO:10); AtSAP12 (GenBank No. At3g28210; SEQ ID NO:11); AtSAP10 (GenBank No. At4g25380; SEQ ID NO:12); OsSAP16 (GenBank No. Os09g38240.1; SEQ ID NO:13); or OsSAP17 (GenBank No. Os09g21710.1; SEQ ID NO:14). In another embodiment, the isolated nucleic acid encodes a polypeptide that confers resistance to an environmental stress.

Disclosed herein is an environmental stress resistant transgenic plant and methods of manufacture thereof. In one embodiment, provided is a transgenic plant transformed with an isolated nucleic acid, the isolated nucleic acid comprising a plant SAP coding sequence operatively linked to a plant-expressible transcription regulatory sequence. The inventors have discovered that the increased expression of a plant SAP gene in a transgenic plant dramatically increases the environmental stress resistance of the transgenic plants. An additional advantage is that the increase in environmental stress resistance also results in increased biomass of the transgenic plants. The environmental or abiotic stresses include environmental stresses, such as, but not limited to, toxic metals, high salt concentrations, drought, cold, heat, and submergence.

In one embodiment, the transgenic plants further comprise an isolated nucleic acid suitable for expression of a coding sequence for an enzyme involved in the biosynthesis of the phytochelatins. Phytochelatins are peptides of higher plants having a general structure of (γ-Glu-Cys)$_n$-Gly, where n equals 2 to 11. Phytochelatins are synthesized in plants in response to the presence of heavy metals and form stable complexes with metal ions. Exemplary phytochelatin biosynthetic enzymes include γ-ECS (γ-glutamylcysteine synthase), GS (glutathione synthase), and PCS (phytochelatin synthase). In one embodiment, both isolated SAP and phytochelatin biosynthetic enzyme recombinant genes (transgenes) are combined in a single plant genome by cotransformation of two constructs, by sequential transformation, or by cross-breeding singly transformed plants, each containing one of the genetic constructs of interest, with selection for progeny having both the SAP coding sequence and the phytochelatin biosynthetic coding sequence. In another embodiment, two or more transgenes are combined in a single plant by conventional breeding and screening (phenotypic or for molecular markers) to obtain the plant that express both the recombinant SAP gene and the recombinant phytochelatin biosynthetic enzyme gene.

In animals, it has been shown that AIRAPs are selectively induced in response to As(III) (Sok et al., 2001). AIRAP mRNA was induced more than 15-fold by As(III) treatment and 5-fold by Zn treatment in mouse epithelial cells. The mouse AIRAP homologous sequences were identified in *Caenorhabditis elegans, Drosophila melanogaster*, and human (Sok et al., 2001). The amino acid sequence alignment of these related proteins revealed the presence of highly conserved motifs with 8 cysteines and histidines repeated twice in the protein. The arrangement of cysteine and histidine residues in these AIRAPs is similar to those known to form metal coordination complex similar to the RING-finger type (Saurin et al., 1996) but does not conform to the strict RING or RING-H2 consensus. These proteins have been shown to protect *Caenorhabditis elegans* and human cells from As(III) toxicity but their exact function is not known. The RNAi knockdown of *C. elegans* homologue of AIRAP, aip-1, lowers the resistance of nematodes to As(III) but did not affect viability without As(III) exposure (Sok et al., 2001)) Immunoprecipitation and cell fractionation experiments in mouse cell indicated that, when induced, AIRAP is present in both the nucleus and the cytoplasm. Further, in vivo cross-linking experiments indicated that AIRAP is associated with RNA (Sok et al., 2002), and hence their name RNA-associated proteins. These results indicate that AIRAP functions in association with RNA, however, their exact function remain unknown so far.

The inventors have discovered plant homologues of AIRAP. The *Arabidopsis* homologues (AtSAP10-14) encode for polypeptides corresponding to 130, 279, 186, 249, and 191 amino acid residues, respectively. The AtAIRAP homologous sequences are also conserved in other plant species such as rice and brassica. The rice homologues (OsSAP16-17) encode for polypeptides corresponding to 290 and 188 amino acid residues, respectively.

The inventors identified a family of 14 and 18 AIRAP homologous proteins in *Arabidopsis* and rice, respectively. These genes encode hypothetical proteins containing A20/AN1 zinc-fingers with unknown functions. Recently, the members of this A20/AN1 type zinc finger protein family were designated as Stress Associated Proteins, SAPs (Vij and Tyagi, 2006). Accordingly, the *Arabidopsis* and rice genes are currently referred to as AtSAPs and OsSAPs, respectively. Table 1 shows the new SAP gene names and the corresponding old AIRAP gene names.

TABLE 1

| Seq ID No: (DNA) | Seq ID No: (protein) | Gene name (Old) | Locus ID | New name |
|---|---|---|---|---|
| 1 | 8 | AtAIRAP1 | At2g41835 | AtSAP11 |
| 2 | 9 | AtAIRAP2 | At3g57480 | AtSAP13 |
| 3 | 10 | AtAIRAP3 | At5g48205 | AtSAP14 |
| 4 | 11 | AtAIRAP4 | At3g28210 | AtSAP12 |
| 5 | 12 | AtAIRAP5 | At4g25380 | AtSAP10 |
| 6 | 13 | OsAIRAP1 | Os07g38240.1 | OsSAP16 |
| 7 | 14 | OsAIRAP2 | Os0921710.1 | OsSAP17 |

In *Arabidopsis* and rice genomes, there are 14 and 18, respectively, A20/AN1 zinc-finger type proteins including the SAP homologues (Jin et al., 2007; Vij and Tyagi, 2006). Out of the 14 reported *Arabidopsis* proteins, 10 are reported to contain A20-AN1 type zinc finger domains and four as AN1 type zinc-finger domains. The *Arabidopsis* AtSAP10-14 and rice OsSAP16-17 proteins disclosed herein are AN1 type zinc finger proteins and contain Cys2-His2 finger motifs. Based on a phylogenetic analysis of the AN1 zinc finger domain, Jin et al., (2007) recently divided all A20/AN1 zinc finger genes into two groups, Type I and Type II. Type I gene contains the traditional pattern, $CX_2CX_{9,12}CX_{1,2}CX_4CX_2HX_5HXC$, whereas, Type II contains the expanded domain, $CX_4CX_2CX_{9,12}CX_{1,2}CX_4CX_2HX_5HXC$ where X represents any amino acid. There are ten members from *Arabidopsis* and fifteen members from rice in the Type I genes group. The Type II genes group includes nine members—three from *Arabidopsis* and two from rice. Type I genes contain one intact A20 type and one AN1 type zinc finger domain, whereas, Type II genes contain two intact AN1 type zinc finger domain and lack A20 type domain (Jin et al., 2007). Based on the phylogenetic analysis of Type II genes, Jin et al. (2007), further divided Type II group into two subclasses—class IIA and class IIB. Class IIA members, in addition to AN1 domain, also contain extra $C_2H_2$ type zinc finger domain at C-terminal. Two *Arabidopsis* SAPs (AtSAP11 and AtSAP13) and the rice OsSAP16 belong to class IIA. The third and fourth *Arabidopsis* protein AtAIRP3 and AtSAP12 represent class IIB because they lack the extra C-terminal $C_2H_2$ type zinc finger domain. There is a striking difference in the structure of A20/AN1 zinc finger genes in plants and animals. Only two human Type I genes have protein structure similar to those of plants and all human/animal Type II genes have protein structures different from those of plants. This led Jin et al. (2007) to conclude that there is a plant-specific protein structure for Type II genes.

Figure 1:
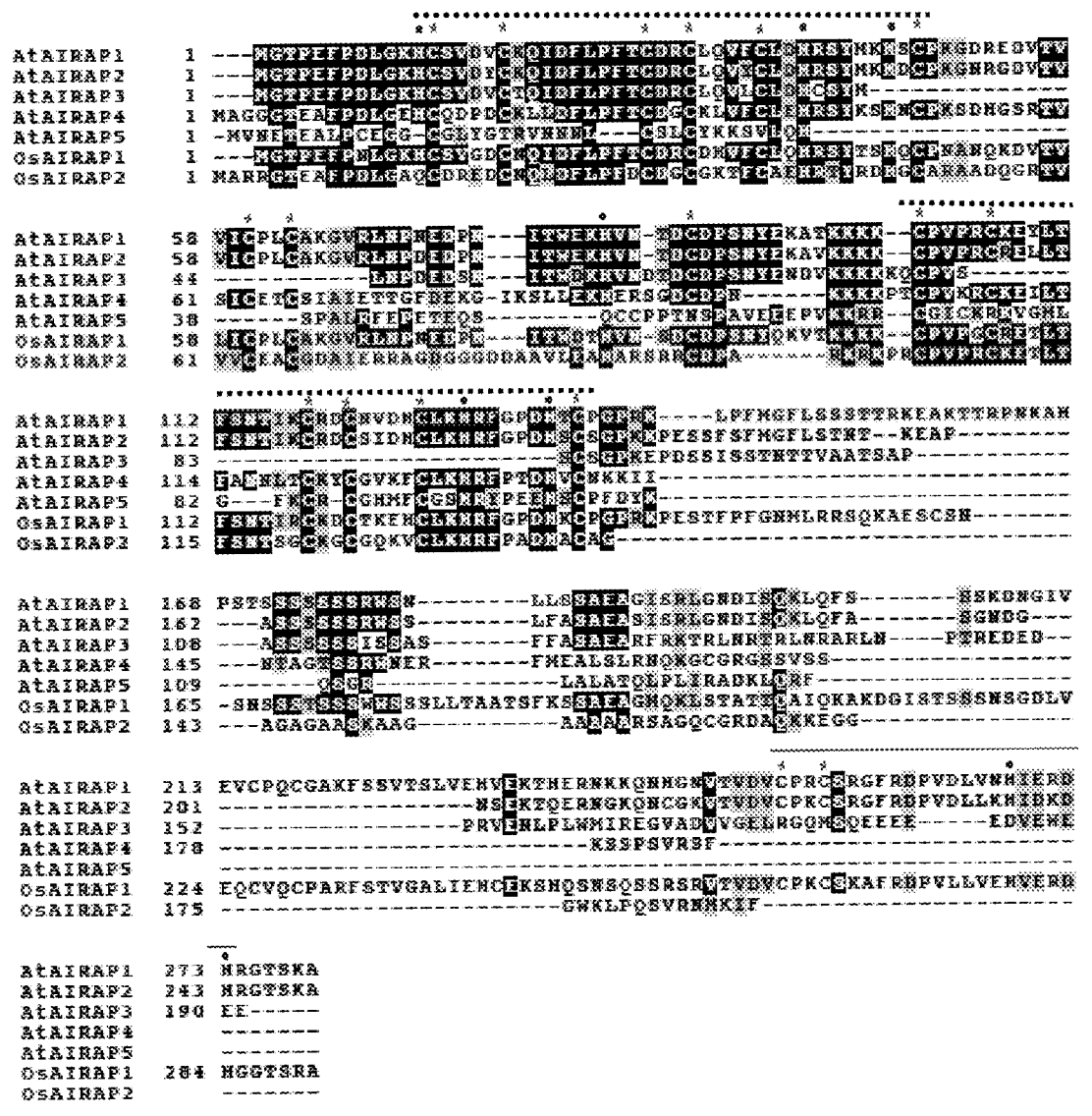

The *Arabidopsis* SAP protein sequences are highly cysteine and histidine-rich and have more than 60% similarity to the animal protein in the conserved sulfur-rich region proposed to bind As(III). As shown in FIG. 1, alignment of the predicted protein sequences of the five *Arabidopsis* SAPs reveal the presence of highly conserved cysteine and histidine repeats arranged in particular configurations. (FIG. 1) For example, the AtSAP11, AtSAP13, AtSAP14, AtSAP12, AtSAP10 sequences contain a distinct pattern of 19, 18, 9, 16, and 12 conserved cysteine residues, respectively.

The inventors have further unexpectedly discovered that plants, such as *Arabidopsis thaliana*, genetically engineered to overexpress a plant SAP gene, demonstrate improved metal resistance. Without being bound by theory, it is hypothesized that the conserved Cys2-His2 zinc finger domains are involved in coordinating and binding metals. According to this model, plants have improved metal resistance because the metals are sequestered in these zinc finger-metal complexes. Similar results are obtainable in other plants, including monocots, dicots and gymnosperms, after stable transformation and regeneration. Suitable plants also include field crops, fruits, and vegetables such as canola, sunflower, tobacco, mustard, crambe, sugar beet, cotton, maize, wheat, barley, rice, sorghum, mangel-wurzels, tomato, mango, peach, apple, pear, strawberry, banana, melon, potato, carrot, lettuce, cabbage, onion, soybean, sugar cane, pea, field beans, poplar, grape, citrus, alfalfa, rye, oats, turf and forage grasses, flax and oilseed rape, nut producing plants, and the like. Suitable plants also include biofuel, biomass, and bioenergy crop plants. Exemplary plants include *Arabidopsis thaliana*, rice (*Oryza sativa*), switchgrass (*Panicum vigratum*), *Brachypodium* spp, corn (*Zea mays*), *Sorghum* spp, barley (*Hordeum vulgare*), wheat (*Triticum aestivum*), *Brassica* spp., and *Crambe abyssinica*.

As used herein, the term "metal resistance" means that a non-naturally occurring organism (e.g., a transgenic plant) is not inhibited by the presence of at least one ionic form of a metal or metalloid at a concentration or amount that inhibits or is toxic to a naturally occurring (wild type) counterpart of the non-naturally occurring organism. It is not intended that the term metal resistance refer to resistance to unlimited metal concentrations, but rather the term is relative in that it relies on comparison to the properties of a parental strain. "Metal" refers to an element classified as a metal or metalloid as well any ionic forms of the metal or metalloid elements. Exemplary metals include arsenic (As), cadmium (Cd), chromium (Cr), lead (Pb), mercury (Hg), nickel (Ni), manganese (Mn), iron (Fe), and zinc (Zn). In one embodiment, a metal resistant organism is resistant to a metal concentration of greater than or equal to about 50 micromolar. Specifically, a metal resistant organism is resistant to a metal concentration of greater than or equal to about 100 micromolar. More specifically, a metal resistant organism is resistant to a metal concentration of greater than or equal to about 500 micromolar. Even more specifically, a metal resistant organism is resistant to a metal concentration of greater than or equal to about 1 millimolar.

In one embodiment, the metal resistant transgenic plant is also resistant to other environmental stresses, including, but not limited to abiotic stresses such as high salt concentration, drought, cold, and submergence. As used herein, the term "stress resistance" means that a non-naturally occurring organism (e.g., a transgenic plant) is not inhibited by an environmental stress that inhibits or is toxic to a naturally occurring (wild type) counterpart of the non-naturally occurring organism. It is not intended that the term stress resistance refer to resistance to unlimited stress (e.g., concentration, temperature, or duration), but rather the term is relative in that it relies on comparison to the properties of a parental strain. Stress refers to environmental conditions such as high salt concentration, drought, cold, and submergence that inhibit growth or are toxic to a wild type plant. In one embodiment, a stress resistant organism is resistant to a one-week exposure to a salt concentration of greater than or equal to about 50 millimolar. Specifically, a stress resistant organism is resistant to a one-week exposure to a salt concentration of greater than or equal to about 100 millimolar. More specifically, a stress resistant organism is resistant to a one-week exposure to a salt concentration of greater than or equal to about 250 millimolar. Even more specifically, a stress resistant organism is resistant to a one-week exposure to a salt concentration of greater than or equal to about 500 millimolar.

An "SAP sequence" is one that encodes a protein capable of mediating resistance to metals or metalloids and their ions, including, but not limited to, arsenic (As), cadmium (Cd), chromium (Cr), lead (Pb), mercury (Hg), nickel (Ni), manganese (Mn), and zinc (Zn). Also within the scope of this definition are variant sequences that encode proteins capable of mediating resistance to metals or metalloids and their ions. Suitable SAP sequences include the Arabidopsis thaliana SAP1-5 sequences and the rice SAP1-2 sequences.

In one embodiment, included herein are isolated SAP nucleic acids. An isolated nucleic acid is a nucleic acid the structure of which is not identical to that of any naturally occurring nucleic acid or to that of any fragment of a naturally occurring genomic nucleic acid spanning more than three separate genes. The term therefore covers, for example, (a) a DNA that has the sequence of part of a naturally occurring genomic DNA molecule but is not flanked by both of the coding or noncoding sequences that flank that part of the molecule in the genome of the organism in that it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transformed or transfected cells, and (iii) cell clones, e.g., as these occur in a DNA library such as a cDNA or genomic DNA library.

In one embodiment, the SAP comprises the Arabidopsis thaliana AtSAP11 sequence (nucleotide sequence SEQ ID NO:1, Accession number NM_180027.1; polypeptide sequence SEQ ID NO:8, Accession number NP_850358.1). In another embodiment, the SAP comprises the AtSAP13 sequence (nucleotide sequence SEQ ID NO:2, NM_115608.3; polypeptide sequence SEQ ID NO:9, Accession number NP_191307.1). In another embodiment, the SAP comprises the AtSAP14 sequence (nucleotide sequence SEQ ID NO:3, Accession number NM_203175.1; polypeptide sequence SEQ ID NO:10, Accession number NP_974904.1). In another embodiment, the SAP comprises the AtSAP12 sequence (nucleotide sequence SEQ ID NO:4, Accession number NM_113740.4; polypeptide sequence SEQ ID NO:11, Accession number NP_189461.1.) In another embodiment, the SAP comprises the AtSAP10 sequence (nucleotide sequence SEQ ID NO:5; Accession number NM_118670.1; polypeptide sequence SEQ ID NO:12; Accession number NP_194268.1.) In another embodiment, the SAP comprises the OsSAP16 sequence (nucleotide sequence SEQ ID NO:6; Accession number gi|133146764; polypeptide sequence SEQ ID NO:13; Accession number gi|133146779.) In another embodiment, the SAP comprises the OsSAP16 sequence (nucleotide sequence SEQ ID NO:7; Accession number gi|149387714; polypeptide sequence SEQ ID NO:14; Accession number gi|140363792.)

An SAP includes an SAP homologous to AtSAP10-14 or OsSAP16-17 so long as the SAP has SAP activity. "Homolog" is a generic term used in the art to indicate a nucleic acid or polypeptide sequence possessing a high degree of sequence relatedness to a subject sequence. Such relatedness may be quantified by determining the degree of identity and/or similarity between the sequences being compared. Falling within this generic term are the terms "ortholog" meaning a nucleic acid or polypeptide that is the functional equivalent of a nucleic acid or polypeptide in another species, and "paralog" meaning a functionally similar sequence when considered within the same species. Paralogs present in the same species or orthologs of the AtACR2 gene in other plant species can readily be identified without undue experimentation, by molecular biological techniques well known in the art. As used herein, AtSAP10-14 and OsSAP16-17 refer to AtSAP10-14 and OsSAP16-17, respectively, as well as their homologs and orthologs.

As used herein, "percent homology" of two amino acid sequences or of two nucleic acid sequences is determined using the algorithm of Karlin and Altschul (1990) *Proc. Natl. Acad. Sci., U.S.A.* 87: 2264-2268. Such an algorithm is incorporated into the NBLAST and XBLAST programs of Altschul et al. (1990) *J. Mol. Biol.* 215: 403-410. BLAST nucleotide searches are performed with the NBLAST program, score=100, word length 12, to obtain nucleotide sequences homologous to a nucleic acid molecule of the invention. BLAST protein searches are performed with the XBLAST program, score=50, word length=3, to obtain amino acid sequences homologous to a reference polypeptide. To obtain gapped alignments for comparison purposes, Gapped BLAST is utilized as described in Altschul et al. (1997) *Nucleic Acids Res.* 25: 3389-3402. When utilizing BLAST and Gapped BLAST programs, the default parameters are typically used. (See http://www.ncbi.nlm.nih.gov)

In addition, nucleic acids that are substantially identical to a nucleic acid encoding an AtSAP10-14 or an OsSAP16-17 polypeptide are included. By "substantially identical" is meant a polypeptide or nucleic acid having a sequence that is at least about 75%, specifically about 85%, more specifically about 90%, and even more specifically about 95% or more identical to the sequence of the reference amino acid or nucleic acid sequence. For polypeptides, the length of the reference polypeptide sequence will generally be at least about 16 amino acids, or specifically at least about 20 amino acids, more specifically at least about 25 amino acids, and most specifically at least about 35 amino acids. For nucleic acids, the length of the reference nucleic acid sequence will generally be at least about 50 nucleotides, specifically at least about 60 nucleotides, more specifically at least about 75 nucleotides, and most specifically at least about 110 nucleotides.

Typically, homologous sequences can be confirmed by hybridization, wherein hybridization under stringent conditions. Using the stringent hybridization (i.e., washing the nucleic acid fragments twice where each wash is at room temperature for 30 minutes with 2× sodium chloride and sodium citrate (SCC buffer; 150 mM sodium chloride and 15 mM sodium citrate, pH 7.0) and 0.1% sodium dodecyl sulfate (SDS); followed by washing one time at 50° C. for 30 minutes with 2× SCC and 0.1% SDS; and then washing two times where each wash is at room temperature for 10 minutes with 2×SCC), homologous sequences can be identified comprising at most about 25 to about 30% base pair mismatches, or about 15 to about 25% base pair mismatches, or about 5 to about 15% base pair mismatches.

Nucleic acids encoding AtSAP10-14 or OsSAP16-17 sequences allow for the preparation of relatively short DNA (or RNA) sequences having the ability to specifically hybridize to such gene sequences. The short nucleic acid sequences may be used as probes for detecting the presence of complementary sequences in a given sample, or may be used as primers to detect, amplify or mutate a defined segment of the DNA sequences encoding an AtSAP10-14 or OsSAP16-17 polypeptide. A nucleic acid sequence employed for hybridization studies may be greater than or equal to about 14 nucleotides in length to ensure that the fragment is of sufficient length to form a stable and selective duplex molecule. Such fragments are prepared, for example, by directly synthesizing the fragment by chemical means, by application of nucleic acid reproduction technology, such as PCR technology, or by excising selected nucleic acid fragments from recombinant plasmids containing appropriate inserts and suitable restriction sites.

The term plant SAP includes nucleic acids that encode the AtSAP10-14 and OsSAP16-17 polypeptides or full-length proteins that contain substitutions, insertions, or deletions into the polypeptide backbone. Related polypeptides are aligned with AtSAP10-14 and OsSAP16-17 by assigning degrees of homology to various deletions, substitutions and other modifications. Homology can be determined along the entire polypeptide or nucleic acid, or along subsets of contiguous residues. The percent identity is the percentage of amino acids or nucleotides that are identical when the two sequences are compared. The percent similarity is the percentage of amino acids or nucleotides that are chemically similar when the two sequences are compared. AtSAP10-14 or OsSAP16-17, and homologous polypeptides are preferably greater than or equal to about 75%, preferably greater than or equal to about 80%, more preferably greater than or equal to about 90% or most preferably greater than or equal to about 95% identical.

A homologous polypeptide may be produced, for example, by conventional site-directed mutagenesis of nucleic acids (which is one avenue for routinely identifying residues of the molecule that are functionally important or not), by random mutation, by chemical synthesis, or by chemical or enzymatic cleavage of the polypeptides.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide that is 50% identical to the reference polypeptide over its entire length. Of course, many other polypeptides will meet the same criteria.

Reference herein to either the nucleotide or amino acid sequence of AtSAP10-14 and OsSAP16-17 also includes reference to naturally occurring variants of these sequences. Non-naturally occurring variants that differ from SEQ ID NOs:1-7 (nucleotide) and 8-14 (amino acid) and retain biological function are also included herein. Preferably the variants comprise those polypeptides having conservative amino acid changes, i.e., changes of similarly charged or uncharged amino acids. Genetically encoded amino acids are generally divided into four families: (1) acidic (aspartate, glutamate); (2) basic (lysine, arginine, histidine); (3) non-polar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. As each member of a family has similar physical and chemical properties as the other members of the same family, it is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting molecule. Whether an amino acid change results in a functional polypeptide can readily be determined by assaying the properties of transgenic plants containing the AtSAP10-14 and OsSAP16-17 derivatives.

Reference to AtSAP10-14 and OsSAP16-17 also refers to polypeptide derivatives of AtSAP10-14 and OsSAP16-17. As used herein, "polypeptide derivatives" include those polypeptides differing in length from a naturally-occurring AtSAP10-14 and OsSAP16-17 and comprising about five or more amino acids in the same primary order as is found in AtSAP10-14 and OsSAP16-17. Polypeptides having substantially the same amino acid sequence as AtSAP10-14 and OsSAP16-17 but possessing minor amino acid substitutions that do not substantially affect the ability of AtSAP10-14 and OsSAP16-17 polypeptide derivatives to interact with AtSAP10-14 and OsSAP16-17-specific molecules, respectively, such as antibodies, are within the definition of AtSAP10-14 and OsSAP16-17 polypeptide derivatives. Polypeptide derivatives also include glycosylated forms, aggregative conjugates with other molecules and covalent conjugates with unrelated chemical moieties.

In one embodiment, the SAP (e.g., AtSAP10-14 and OsSAP16-17 genes or their homologs) are expressed in vectors suitable for in vivo expression such as, for example, plant expression systems. The SAP nucleic acids are inserted into a recombinant expression vector or vectors. The term "recombinant expression vector" refers to a plasmid, virus, or other means known in the art that has been manipulated by insertion or incorporation of the SAP genetic sequence. The term "plasmids" generally is designated herein by a lower case p preceded and/or followed by capital letters and/or numbers, in accordance with standard naming conventions that are familiar to those of skill in the art. Plasmids disclosed herein are either commercially available, publicly available on an unrestricted basis, or can be constructed from available plasmids by routine application of well-known, published procedures. Many plasmids and other cloning and expression vectors are well known and readily available, or those of ordinary skill in the art may readily construct any number of other plasmids suitable for use. These vectors are transformed into a suitable host cell to form a host cell vector system for the production of a polypeptide.

The term recombinant nucleic acid or nucleic acid refers to a nucleic acid that is made by the combination of two otherwise separated segments of sequence accomplished by the artificial manipulation of isolated segments of nucleic acids by genetic engineering techniques or by chemical synthesis. In so doing, one may join together nucleic acid segments of desired functions to generate a desired combination of functions.

The term transgene refers to an isolated nucleic acid or nucleic acid that comprises a coding sequence encoding a protein or RNA molecule.

The SAP nucleic acids are inserted into a vector adapted for expression in a plant, bacterial, yeast, insect, amphibian, or mammalian cell that further comprises the regulatory elements necessary for expression of the nucleic acid molecule in the plant, bacterial, yeast, insect, amphibian, or mammalian cell operatively linked to the nucleic acid molecule encoding SAP. Suitable vectors for plant expression include T-DNA vectors. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns (if introns are present), maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter. By "promoter" is meant minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included. If a promoter is inducible, there are sequences present that mediate regulation of expression so that the associated sequence is transcribed only when an inducer (e.g., light) is available to the plant or plant tissue. An exemplary promoter is the *Arabidopsis* ACT2 promoter that is constitutively active and provides high levels of expression of an associated coding sequence.

Other suitable expression control sequences include 3' untranslated sequences located downstream of an associated coding sequence. An exemplary 3' untranslated sequence is that from the ACT2 gene of *Arabidopsis*.

With respect to a coding sequence, the term "plant-expressible" means that the coding sequence (nucleotide sequence) can be efficiently expressed by plant cells, tissue and/or whole plants. As used herein, a plant-expressible coding sequence has a GC composition consistent with acceptable gene expression in plant cells, a sufficiently low CpG content so that expression of that coding sequence is not restricted by plant cells, and codon usage that is consistent with that of plant genes. Where it is desired that the properties of the plant-expressible metal resistance gene are identical to those of the naturally occurring metal resistance gene, the plant-expressible homolog will have a synonymous coding sequence or a substantially synonymous coding sequence. A substantially synonymous coding sequence is one in that there are codons that encode similar amino acids to a comparison sequence, or if the amino acid substituted is not similar in properties to the one it replaces, that change has no significant effect on enzymatic activity for at least one substrate of that enzyme. As discussed herein, it is well understood that in most cases, there is some flexibility in amino acid sequence such that function is not significantly changed. Conservative changes in amino acid sequence, and the resultant similar protein can be readily tested using procedures such as those disclosed herein. Where it is desired that the plant-expressible gene have different properties, there can be variation in the amino acid sequence as compared to the wild type gene, and the properties of metal resistance can be readily determined as described herein.

"Plant-expressible transcriptional and translational regulatory sequences" are those that can function in plants, plant tissue and/or plant cells to effect the transcriptional and translational expression of the nucleotide sequences with that they are associated. Included are 5' sequences that qualitatively control gene expression (turn on or off gene expression in response to environmental signals such as light, or in a tissue-specific manner) and quantitative regulatory sequences that advantageously increase the level of downstream gene expression. An example of a sequence motif that serves as a translational control sequence is that of the ribosome binding site sequence. Polyadenylation signals are examples of transcription regulatory sequences positioned downstream of a target sequence. Exemplary flanking sequences include the 3' flanking sequences of the nos gene of the *Agrobacterium tumefaciens* Ti plasmid.

The plant-expressible transcription regulatory sequence optionally comprises a constitutive promoter to drive gene expression throughout the whole plant or a majority of plant tissues. In one embodiment, the constitutive promoter drives gene expression at a higher level than the endogenous plant gene promoter. In one embodiment, the constitutive promoter drives gene expression at a level that is at least two-fold higher, specifically at least five-fold higher, and more specifically at least ten-fold higher than the endogenous plant gene promoter. Suitable constitutive promoters include plant virus promoters such as the cauliflower mosaic virus (CaMV) 35S and 19S promoters. An exemplary plant virus promoter is the cauliflower mosaic virus 35S promoter. Suitable constitutive promoters further include promoters for plant genes that are constitutively expressed such as the plant ubiquitin, Rubisco, and actin promoters such as the ACT 1 and ACT2 plant actin genes. Exemplary plant gene promoters include the ACT2 promoter from *Arabidopsis* (SEQ ID. NO:15) and the ACT1 promoter from rice (GenBank Accession no. 544221.1; SEQ ID. NO:16).

Where a regulatory element is to be coupled to a constitutive promoter, generally a truncated (or minimal) promoter is used, for example, the truncated 35S promoter of Cauliflower Mosaic Virus. Truncated versions of other constitutive promoters can also be used to provide CAAT and TATA-homologous regions; such promoter sequences can be derived from those of *Agrobacterium tumefaciens* T-DNA genes such as nos, ocs and mas and plant virus genes such as the CaMV 19S gene or the ACT2 gene of *Arabidopsis*. Translational control sequences specifically exemplified herein are the nucleotides between 8 and 13 upstream of the ATG translation start codon for bacterial signals and from nucleotides 1 to 7 upstream of the ATG translation start codon for plants.

A minimal promoter contains the DNA sequence signals necessary for RNA polymerase binding and initiation of transcription. For RNA polymerase II promoters, the promoter is identified by a TATA-homologous sequences motif about 20 to 50 base pairs upstream of the transcription start site and a CAAT-homologous sequence motif about 50 to 120 base pairs upstream of the transcription start site. By convention, the nucleotides upstream of the transcription start with increasingly large numbers extending upstream of (in the 5' direction) from the start site. In one embodiment, transcription directed by a minimal promoter is low and does not respond either positively or negatively to environmental or developmental signals in plant tissue. An exemplary minimal promoter suitable for use in plants is the truncated CaMV 35S promoter, that contains the regions from −90 to +8 of the 35S gene. Where high levels of gene expression are desired, transcription regulatory sequences that upregulate the levels of gene expression may be operatively linked to a minimal promoter is used thereto. Such quantitative regulatory sequences are exemplified by transcription enhancing regulatory sequences such as enhancers.

In one embodiment, the plant-expressible transcription regulatory sequence comprises a tissue or organ-specific promoter to drive gene expression in selected organs such as roots or shoots and tissues therein. In one embodiment, the organ-specific promoter drives gene expression in below ground tissues such as roots and root hairs. In one embodiment, the organ-specific promoter drives gene expression in above ground tissues such as shoots and leaves. An exemplary leaf-specific promoter is the SRS1 promoter (SEQ ID. NO:17). In one embodiment, the organ-specific promoter drives gene expression in floral and reproductive tissues.

The plant-expressible transcription regulatory sequence optionally comprises an inducible promoter to drive gene expression in response to selected stimuli. Suitable inducible promoters include a light inducible promoter such as the SRS1 promoter, arsenic inducible promoters such as the OsACR2 promoter, and the chlorophyll A/B binding protein light-inducible transcription regulatory sequences.

The choice of vector used for constructing the recombinant DNA molecule depends on the functional properties desired, e.g., replication, protein expression, and the host cell to be transformed. In one embodiment, the vector comprises a prokaryotic replicon, i.e., a DNA sequence having the ability to direct autonomous replication and maintenance of the recombinant DNA molecule extrachromosomally when introduced into a prokaryotic host cell, such as a bacterial host cell. In addition, the vector may also comprise a gene whose expression confers a selective advantage, such as a drug resistance, to the bacterial host cell when introduced into those transformed cells. Suitable bacterial drug resistance genes are those that confer resistance to ampicillin or tetracycline, among other selective agents. The neomycin phosphotransferase gene has the advantage that it is expressed in eukaryotic as well as prokaryotic cells.

Vectors typically include convenient restriction sites for insertion of a recombinant DNA molecule. Suitable vector plasmids include pUC8, pUC9, pBR322, and pBR329 available from BioRad Laboratories (Richmond, Calif.) and pPL, pK and K223 available from Pharmacia (Piscataway, N.J.), and pBLUESCRIPT® and pBS available from Stratagene (La Jolla, Calif.). Suitable vectors include, for example, Lambda phage vectors including the Lambda ZAP vectors available from Stratagene (La Jolla, Calif.). Other exemplary vectors include pCMU. Other appropriate vectors may also be synthesized, according to known methods; for example, vectors pCMU/K$^b$ and pCMUII which are modifications of pCMUIV.

Suitable expression vectors capable of expressing an isolated nucleic acid sequence in plant cells and capable of directing stable integration within the host plant cell include vectors derived from the tumor-inducing (Ti) plasmid of Agrobacterium tumefaciens, and several other expression vector systems known to function in plants. See for example, Verma et al., No. WO87/00551, incorporated herein by reference.

Expression and cloning vectors optionally contain a selectable marker, that is, a gene encoding a protein necessary for the survival or growth of a host cell transformed with the vector. Although such a marker gene may be carried on another nucleic acid sequence co-introduced into the host cell, it is most often contained on the cloning vector. Only those host cells into which the marker gene has been introduced will survive and/or grow under selective conditions. Suitable selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend, in part, on the host cell. In one embodiment, the metal resistance coding sequence itself is used as a selectable marker to select transformants on medium supplemented with an appropriate concentration of arsenic.

In one embodiment, the plant SAP coding sequence is cloned into a vector suitable for expression in Arabidopsis and rice under the control of different constitutive promoters including the CaMV 35S promoter and the actin promoters from Arabidopsis and rice. In one embodiment, the plant SAP coding sequence is regulated by an organ or tissue-specific or an inducible promoter. An exemplary tissue-specific promoter is the leaf-specific SRS1 promoter (SEQ ID. NO:14). In one embodiment, the plant SAP coding sequence is cloned into a plant expression cassette construct or vector comprising a promoter, convenient cloning sites and the nos transcription terminator (NOSt).

Transformation of a host cell with an expression vector or other DNA is carried out by conventional techniques as are well known to those skilled in the art. By "transformation" is meant a permanent or transient genetic change induced in a cell following incorporation of new DNA (i.e., DNA exogenous to the cell). Where the cell is a plant cell, a permanent genetic change is generally achieved by introduction of the DNA into the genome of the cell. By "transformed cell" or "host cell" is meant a cell (e.g., prokaryotic or eukaryotic) into which (or into an ancestor of which) has been introduced, by means of recombinant DNA techniques, a DNA molecule encoding an SAP (e.g., an AtSAP10-14 or OsSAP16-17 polypeptide), or fragment thereof.

Recombinant host cells, in the present context, are those that have been genetically modified to contain an isolated DNA molecule. The DNA can be introduced by a means that is appropriate for the particular type of cell, including without limitation, transfection, transformation, lipofection, or electroporation.

Also included herein are transgenic plants that have been transformed with an SAP gene. A "transgenic plant" is one that has been genetically modified to contain and express recombinant DNA sequences, either as regulatory RNA molecules or as proteins. As specifically exemplified herein, a transgenic plant is genetically modified to contain and express a recombinant DNA sequence operatively linked to and under the regulatory control of transcriptional control sequences that function in plant cells or tissue or in whole plants. As used herein, a transgenic plant also encompasses progeny of the initial transgenic plant where those progeny contain and are capable of expressing the recombinant coding sequence under the regulatory control of the plant-expressible transcription control sequences described herein. Seeds containing transgenic embryos are encompassed within this definition.

Individual plants within a population of transgenic plants that express a recombinant gene may have different levels of gene expression. The variable gene expression is due to multiple factors including multiple copies of the recombinant gene, chromatin effects, and gene suppression. Accordingly, a phenotype of the transgenic plant may be measured as a percentage of individual plants within a population. In one embodiment, greater than or equal to about 25% of the transgenic plants express the phenotype. Specifically, greater than or equal to about 50% of the transgenic plants express the phenotype. More specifically, greater than or equal to about 75% of the transgenic plants express the phenotype. In one embodiment, the phenotype is metal resistance. In another embodiment, the phenotype is metal resistance and stress resistance.

The transgenic plant is transformed with an isolated nucleic acid or nucleic acid molecule comprising a plant SAP coding sequence operatively linked to a plant-expressible transcription regulatory sequence. Exemplary plant SAP genes include *Arabidopsis* AtSAP10-14 (SEQ ID NOs:1-5) and rice OsSAP16-17 (SEQ ID NOs:6-7). The transgenic plant expresses a plant SAP. Suitable plant SAPs include SAPs from *Arabidopsis*, rice, and *Brassica* plants. Exemplary plant SAPs include *Arabidopsis* AtSAP10-14 (SEQ ID NOs: 8-12) and rice OsSAP16-17 (SEQ ID NOs:13-14).

The present inventors have transformed plants with recombinant DNA molecules that encode a plant SAP. Transgenic plants and plant cells expressing the recombinant plant SAP gene are more resistant to metals than wild type control plants. In one embodiment, greater than or equal to about 25% of the transgenic plants are resistant to a concentration of metal that is lethal to wild type control plants. Specifically, greater than or equal to about 50%, and more specifically, greater than or equal to about 75%, of the transgenic plants are resistant to a concentration of metal that inhibits growth in wild type control plants.

Transgenic plants and plant cells expressing the recombinant plant SAP gene are more resistant to environmental stresses than wild type control plants. In one embodiment, greater than or equal to about 25% of the transgenic plants are resistant to an environmental stress that inhibits growth in wild type control plants. Specifically, greater than or equal to about 50%, and more specifically, greater than or equal to about 75%, of the transgenic plants are resistant to an environmental stress that inhibits growth in wild type control plants.

The increase in metal resistance in the transgenic plants also leads to increased biomass when the transgenic plants are grown in the presence of a concentration of metal that inhibits growth in wild type control plants. The term "biomass" refers to the biological material in plants and includes internal plant structures that comprise dead cells, such as xylem. In one embodiment, biomass is measured by the dry weight of a plant. In one embodiment, the total biomass of the transgenic plant is greater than or equal to about 100%; specifically, greater than or equal to about 250%; and more specifically, greater than or equal to about 500% of the total biomass of wild type control plants when grown in the presence of a concentration of metal that inhibits growth in wild type control plants.

A recombinant DNA construct including a plant-expressible gene or other DNA of interest is inserted into the genome of a plant by a suitable method. Suitable methods include, for example, *Agrobacterium tumefaciens*-mediated DNA transfer, direct DNA transfer, liposome-mediated DNA transfer, electroporation, co-cultivation, diffusion, particle bombardment, microinjection, gene gun, calcium phosphate coprecipitation, viral vectors, and other techniques. Suitable plant transformation vectors include those derived from a Ti plasmid of *Agrobacterium tumefaciens*. In addition to plant transformation vectors derived from the Ti or root-inducing (Ri) plasmids of *Agrobacterium*, alternative methods can be used to insert DNA constructs into plant cells. A transgenic plant can be produced by selection of transformed seeds or by selection of transformed plant cells and subsequent regeneration.

Techniques are well known to the art for the introduction of DNA into monocots as well as dicots, as are the techniques for culturing such plant tissues and regenerating those tissues. Monocots that have been successfully transformed and regenerated include wheat, corn, rye, rice and asparagus. For efficient regeneration of transgenic plants, it is desired that the plant tissue used in the transformation possess a high capacity to produce shoots. For example, Aspen stem sections have good regeneration capacity. Poplars have been successfully transformed and regenerated as have cottonwoods.

In one embodiment, a recombinant DNA, such as a transgene construct, is introduced into rice plants. Transformed rice cells are selected and regenerated into transgenic rice plants. In one embodiment, transformed rice cells are selected on media containing an appropriate antibiotic. The rice cells are induced to form a somatic embryogenic callus. The callus is treated with the appropriate reagents such as plant hormones to induce the formation of root and shoot tissue. In this manner, transgenic rice plants can be regenerated from the callus derived from transformed rice cells.

In one embodiment, the plant SAP coding sequence is subcloned under the control of the soybean plant ribulose biphosphate carboxylase (Rubisco) small subunit promoter SRS1 and the 3' nos terminator in pBluescript®. This coding sequence and promoter are previously shown to be strongly transcriptionally induced in leaves by light. Expression directed by this promoter is very low in roots. The entire chimeric gene including the SRS1 promoter, the SAP coding sequence, and the 3' nos transcription terminator sequence, is subcloned into the plant expression T-DNA binary vector pBIN19, that has the selectable kanamycin-resistance marker (NPTII). *A. thaliana* is transformed using vacuum infiltration technology, and the T1 generation seeds are screened for kanamycin resistance. Transgenic plants transformed with an isolated SAP nucleic acid are produced. In one embodiment, the plant also expresses a phytochelatin biosynthetic enzyme coding sequence, e.g., γ-ECS, PS and/or GS.

The transgenic plant optionally further comprises an isolated nucleic acid suitable for expression of a phytochelatin biosynthetic enzyme coding sequence. In another embodiment, the arsenic-resistant transgenic plants also overexpress thiol-rich peptides like glutathione and phytochelatins to further improve arsenic tolerance. Phytochelatins (PCs) are small peptides that are synthesized non-ribosomally from common amino acid precursors in a three-step enzymatic pathway. Suitable genes that encode phytochelatins include the prokaryotic gamma-glutamylcysteine synthase (γECS) and glutathione synthase (GS) genes and the eukaryotic phytochelatin synthase (PCS) genes. Exemplary phytochelatin genes include the *E. coli* γECS (GenBank Accession no. X03954; SEQ ID NO. 18) and GS (GenBank Accession no. 28377; SEQ ID NO. 19) genes and the PCS genes from fission yeast (*Schizosaccharomyces pombe*) (GenBank Accession no. 28377; SEQ ID NO. 20). In one embodiment, the phytochelatin biosynthetic enzyme coding sequence is greater than or equal to about 75%, 85%, 90% or 95% homologous with a sequence selected from the group consisting of SEQ ID NO:18, SEQ ID NO:19, and SEQ ID NO:20, wherein the phytochelatin biosynthetic enzyme coding sequence has phytochelatin biosynthesis activity. Plants that co-express a phytochelatin synthetic gene such as γECS, GS and PCS together with an SAP gene are further improved in metal resistance. In one embodiment, phytochelatin biosynthetic genes are overexpressed in roots. Without being bound by theory, it is believed that by overexpressing phytochelatin biosynthetic genes in roots, the thiol-rich peptides will bind arsenite generated in roots and thus improve arsenic tolerance and further prevent the movement of arsenic to the aboveground tissues.

In one embodiment, the levels of PC pathway intermediates (gamma-EC, GSH and PC) are expressed at a level in excess of 1% of the total cell protein. In this example, three vector systems are used for all three PC synthesizing enzymes in order to compare their activity and to avoid potential co-suppression problems. For strong constitutive expression and as an alternative promoter to the CaMV 35S promoter, a novel actin promoter expression vector, ACT2pt was developed. The ACT2pt comprises the promoter (p) and terminator (t) from the constitutive ACT2 gene. In controlled experiments with 30 independent ACT2pt/reporter lines and 30 independent 35Sp/reporter lines, the ACT2pt vector gives about 5-10 times higher levels of reporter expression than the 35Sp vector. In several independent experiments using the ACT2pt vector, co-suppression of the endogenous ACT2 gene or the transgene was not observed, even when multiple copies are present. While a plant with low levels of ACT2pt driven expression was not obtained, approximately 10-20% of the 35Sp plants had no detectable reporter expression. Furthermore, the lowest ACT2pt plants are equivalent to the highest 35Sp plants. This apparent insensitivity to cosuppression offers a significant advantage in the multigene strategy being used.

In one embodiment, the nucleic acids encoding thiol-rich peptides are modified by PCR to comprise appropriate sites for cloning to make in-frame translational fusions with actin and SRS1 light regulated promoters. In one embodiment, the nucleic acids are modified for detection in *E. coli* and plants. Monoclonal antibodies specific to AtACR2, γECS, GS, and PCS (fission yeast) proteins have been generated to monitor protein expression. The *Arabidopsis* PCS protein was tagged with an HA (hemagglutinin) epitope to allow monitoring with a commercially available HA-specific antibody. All four proteins confer increased metal tolerance to *E. coli*, when expressed under the control of the lac promoter in pBluescript® vectors. In one embodiment, all four genes are derived from plants including, for example, *Arabidopsis* and rice. Without being bound by theory, it is believed that thiol-rich peptides such as glutathione and phytochelatins, bind arsenic and contribute to arsenic tolerance and accumulation. It is believed that the GS-As and PC-As complexes are pumped into vacuoles for storage, thus improving arsenic tolerance.

In one embodiment, the transgenic plants overexpress a plant SAP and a thiol-rich peptide to synergistically improve metal resistance. The overexpression of the plant SAP improves the As(III) binding capacity of the plant cells while the overexpression of the thiol-rich peptides provide thiol sinks for As(III). For example, the transgenic plant co-overexpresses heterologous PC synthetic genes and plant SAP. In one embodiment, the transgenic plant overexpresses the heterologous PC synthetic genes and plant SAP in a tissue-specific manner. Suitable tissues include, for example, roots, leaves, shoots, stems, and seeds.

In one embodiment, transgenic plants are transformed with vectors that provide overexpression of thiol-rich peptides. For example, the ACT2pt vector has been used to drive exceptionally high levels of constitutive transgenic expression of GS throughout the plant. The ACT2pt vector may further contain intron (IVSL) that enhances expression 20-fold. The ACT2 poly(A) region (Act2t) ensures efficient transcription termination, and it contains multiple polyadenylation sites.

The following examples are provided for illustrative proposes and are not intended to limit the scope of the invention as claimed herein. Any variations in the exemplified compositions and methods, that occur to the skilled artisan, are intended to fall within the scope of the present invention.

EXAMPLES

Plasmids

The pBluescript® SK (−) plasmid (Stratagene, La Jolla, Calif.) and two T-DNA vectors, promoterless binary vectors pBIN19 (Clontech, Palo Alto, Calif.) and pCambia (Cambia, Canberra, Australia), that are designed for expressing genes under a promoter of interest by *Agrobacterium*-mediated transformations, are obtained commercially.

Example 1

Cloning SAP Genes

Various plant databases are searched for genes encoding amino acid sequence homologs of the previously described *C. elegans* aip-1 SAP. Sequences that are the likely plant homologs of the aip-1 protein sequence are identified. Five homologous genes are identified in *A. thaliana* (Columbia ecotype) and two genes are identified in rice (*Oryza sativa* (japonica cultivar)). Three of the putative As(III)-binding proteins from *Arabidopsis*, AtSAP11 (SEQ ID NO:8), AtSAP13 (SEQ ID NO:9), AtSAP12 (SEQ ID NO:11), and the two putative As(III)-binding proteins from rice, OsSAP16 (SEQ ID NO:13) and OsSAP17 (SEQ ID NO:14) have two conserved AN1 zinc finger domains and a $C_2H_2$ domain. High sequence homology among these amino acid sequences and specific arrangements of conserved Cys and His residues suggest that their functions are well conserved. These *Arabidopsis* and rice SAP protein sequences are highly cysteine and histidine-rich and have more than 60% similarity to the animal protein in the conserved sulfur-rich region thought to bind As(III). Alignment of the predicted protein sequences of all AtSAPs and rice OsSAP16 revealed the presence of highly conserved cysteine and histidine repeats arranged in particular configurations. For example, *Arabidopsis* AtSAP11 sequences contain a distinct pattern of 19 conserved cysteine residues in a 279 amino acids protein and 18, 9, 16, and 12 conserved cysteine residues in AtSAP13, AtSAP14, AtSAP12, and AtSAP10 proteins, respectively. Rice OsSAP16 contains 21 cysteine and 10 histidine conserved residues. These Cys- and His-residues are arranged in specific orders that form typical metal-binding domains. These proteins have several $CX_2C$, $CX_4C$, $CX_2CX_4C$ and $CXHX_5HXC$ domains, which may bind As(III) and other heavy metals, and thus provide resistance. The phylogenetic analysis of several SAP proteins show that *Arabidopsis* AtSAP11, AtSAP13, and rice OsSAP16 are closely related to each other, whereas, AtSAP14 and AtSAP12 are separated from this group and is distantly related. The AtSAP11, AtSAP13 and OsSAP16 have extended C-terminal where they contain extra $C_2H_2$ domain. The $C_2H_2$ domain is missing in AtSAP14 and AtSAP12 protein sequences. AtSAP14 and AtSAP12 are tested in order to determine if SAPs that lack the C-terminal $C_2H_2$ type zinc finger domain have different functions than other SAPs.

The *Arabidopsis* SAP sequences are cloned into the multiple cloning site region of pBluescript® II SK (Stratagene) to make a bacterial expression plasmid pBS/AtSAP. For plant expression, the plant SAP sequences are subcloned under the regulatory control of the *Arabidopsis* actin ACT2 promoter and the nopaline synthase (nos) 3' terminator to create pACT2p/SAP. The entire cassette containing the promoter, AtACR2 coding sequence and nos 3' terminator, is subcloned into the *Agrobacterium* pBIN19 Ti vector for transformation into plants.

The *Arabidopsis* AtSAP13 gene is amplified and cloned from *Arabidopsis* shoot and root cDNA libraries. The *Arabidopsis* shoot and root cDNA libraries are made after 12 and 24 hrs induction with 150 micromolar sodium arsenate and 40 micromolar sodium arsenite. AtSAP13 is PCR amplified using sense primer, 5'-TACGTCGGATC-CTAAGGAGGATAGACCATGGGAACTCCAGAATTTC CA GATCTGGGTA-3' (SEQ ID NO:23) and the antisense primer, 5'-TAGCTGGAGCTCAAGCTTCTCGAGCTAG-GCTTTAGAAGTGCCACGATGAT CCTTAT-3' (SEQ ID NO:24). The *Arabidopsis* AtSAP11, AtSAP14, AtSAP12, and AtSAP10 genes are amplified and cloned using similar strategies. The PCR is carried out as 1 cycle at 94° C. for 2 min followed by 40 cycles with denaturing, annealing and extending temperatures and times of 94° C. for 1 min, 55° C. for 1 min and 72° C. for 1 min with an additional extension cycle of 72° C. for 10 min. The amplified fragment corresponding to each gene is gel extracted and then cloned into TOPO TA cloning vector (Invitrogen). The isolated plasmid is sequenced and nucleotide sequences are analyzed and confirmed using Sequencher (GeneCode Corporation)

```
AtSAP11 forward (sense) primer
                                         (SEQ ID NO: 21)
5'-TACGTCGAATTCAGGAGGTAGACCATGGGGACTCCGGAATT-3';

reverse (anti-sense) primer
                                         (SEQ ID NO: 22)
5'-TAGCTGGTCGACAAGCTTCTATGCTTTCGAAGTGCCT-3'.

AtSAP14 forward (sense) primer
                                         (SEQ ID NO: 25)
5'-TACGTCGAATTCAGGAGGTAGACCATGGGGACTCCGGAATT-3';

reverse (anti-sense) primer
                                         (SEQ ID NO: 26)
5'-TAGCTGGTCGACAAGCTTTTATTCTTCTTCCCATTCAACAT-3'.

AtSAP12 forward (sense) primer
                                         (SEQ ID NO: 27)
5'-TACGTCGGATCCAGGAGGTAGACCATGGCAGGAGGAGGAACAGAAG
CGT-3';

reverse (anti-sense) primer
                                         (SEQ ID NO: 28)
5'-TAGCTGGAATTCCTAAAACGATCTAACTGATGGT-3'.

AtSAP10 forward (sense) primer
                                         (SEQ ID NO: 29)
5'-TACGTCGGATCCAGGAGGTAGACCATGGTGAACGAAACAGAAGCA
T-3';

reverse (anti-sense) primer
                                         (SEQ ID NO: 30)
5'-TAGCTGCTCGAGAAGCTTCTAAAACCTCTGCAACTTGTCA-3'.
```

For overexpression of AtSAP13 in plants, the NcoI-XhoI fragment of this gene is cloned under a strong constitutive expression vector cassette, pACT2pt. The expression vector pACT2pt has *Arabidopsis* ACT2 gene promoter and ACT2 gene terminator. The KpnI-SacI fragment containing the entire gene cassette (ACT2pt/AtSAP) is taken out and subcloned into pBIN19 binary vector for transformation into *Agrobacterium* strain C58. The *Arabidopsis* plants are transformed with this construct via standard flower dip using vacuum infiltration. The kanamycin resistant transgenic plants are selected on MS media supplemented with kanamycin. The cloning strategy for AtSAP13 is depicted schematically in FIG. 2. The other AtSAP genes are subcloned into suitable vector cassettes using similar strategies.

The rice OsSAP16 gene is amplified and cloned from rice cDNA libraries. The rice shoot and root cDNA libraries are made after 24 h induction with 300 micromolar sodium arsenate and 100 micromolar sodium arsenite. The 290 amino acid OsSAP16 gene is PCR amplified using sense primer, 5'-TACGTCGGATCCGGACTAAAGGAGGC-CATGGGGACGCCGGAGTTCCCCA-3' (SEQ ID NO:31) and the antisense primer, 5'-TAGCTGCTCGAGC-TACGCTCTTGACGTTCCTCCGTGGTCCCTCT-3' (SEQ ID NO:32). The PCR is carried out as 1 cycle at 94° C. for 2 min followed by 40 cycles with denaturing, annealing and extending temperatures and times of 94° C. for 1 min, 55° C. for 1 min and 72° C. for 2 min with an additional extension cycle of 72° C. for 10 min. The PCR amplified OsSAP16 gene is cloned in pBluescriptII SK using BamHI-XhoI combination of restriction enzymes. For over expression of OsSAP in plants, the NcoI-XhoI fragment of this gene is subcloned into an expression vector pACT1p/NOSt. The expression vector pACT1p/NOSt has the rice ACT1 gene promoter and NOS gene terminator. The KpnI-SacI fragment containing the entire gene cassette (ACT1p/OsSAP16/NOSt) is isolated and subcloned into the pCambia binary vector for transformation into *Agrobacterium* strain LBA4404. OsSAP17 is cloned and amplified using a similar strategy. The OsSAP17 forward primer is 5'-TACGTCGGATCCGGACTAAAGGAGGC-CATGGCGCGGCGGGGCACGGA-3' (SEQ ID NO:33) and the OsSAP17 forward primer is 5'-TAGCTGCTCGAGTCA-GAAAATCTTCATGTTT-3' (SEQ ID NO:34).

Example 2

Cloning γ-ECS, GS, and PS for Bacterial Expression

The γ-ECS (GenBank Accession no. X03954; SEQ ID NO. 18) and GS (GenBank Accession no. 28377; SEQ ID NO. 19) genes are amplified by PCR, using synthetic primers, from genomic DNA of *E. coli* SK1592. The fission yeast *Schizosaccharomyces pombe* PS gene (GenBank Accession no. Z68144; SEQ ID NO. 20) is amplified from a plasmid PsPC/YES clone provided by Julian Schroeder (University of California, San Diego, Calif.). The two oligonucleotide primers for each gene add synthetic flanking sequences for cloning and bacterial expression. The sense primers contain restriction endonuclease cloning sites XhoI and NcoI, a TAA stop codon, and bacterial translation signals. The antisense primers contain cloning sites BamHI and HindIII. The PCR products encoding all three genes are cloned first into the XhoI/BamHI replacement region of pBluescript® KS(II) (Stratagene, La Jolla, Calif.) and electroporated into *E. coli* strain Top10F (Invitrogen, Carlsbad, Calif.). The fidelity of the amplified coding sequences are confirmed by sequencing. To express higher levels of protein, the three genes are subcloned into the NdeI (blunt end)/BamHI replacement region of the expression vector pET15b (Novagen, Madison, Wis.) using post-ligation-digestion with XhoI to select against the parent pET15b vector. These plasmids are expressed in *E. coli* strain BL121 (Novagen) as per the manufacturer's instructions.

Example 3

Construction of Transgenic *Arabidopsis* Plants

Plasmid pBIN/AtSAP13, carrying the chimeric plant SAP gene (ACT2p:AtSAP13:ACT2 3'), is electroporated into cells of the C58 *Agrobacterium tumefaciens* strain (GIBCO/BRL, Gaithersburg, Md.). Transformants are verified by using Southern blotting and/or PCR and cultured in YEP medium (10 g/liter Bacto peptone (Difco, Detroit, Mich.)/10 g/liter yeast extract/5 g/liter NaCl) in the presence of streptomycin and kanamycin to maintain the T-DNA and pBIN19 plasmids, respectively. Wild type *A. thaliana* (ecotype Columbia) plants are transformed with the recombinant *A. tumefaciens* strains using the vacuum infiltration procedure.

Example 4

Construction of Transgenic Japonica Rice Plants

Mature japonica cv. Nipponbare rice seeds are dehusked, surface sterilized and placed onto callus induction medium. The callus tissue derived from the mature embryos are used as the starting material for transformation. *Agrobacterium tumefaciens* strain LBA4404 contained the standard binary vector pCAMBIA1300 harboring the AtACR2 gene under rice ACT1 promoter and nos terminator. The plant selectable marker gene hygromycin phosphotransferase (hpt) is driven by the cauliflower mosaic virus (CaMV) promoter.

Media:
  Callus induction medium: 30 g/L sucrose, N6 salts and vitamins, 1 g/L casein hydrolysate, 0.5 g/L L-proline, 0.5 g/L glutamine, 2 mg/L 2,4-D and 4 g/L gelrite (pH 5.8).
  Regeneration medium: 30 g/L sucrose, MS salts and vitamins, 1 g/L casein hydrolysate, 2 mg/L BAP, 0.5 mg/L NAA and 4 g/L gelrite (pH 5.8).
  Rooting and shoot multiplication medium: 30 g/L sucrose, MS salts and vitamins and 4 g/L gelrite (pH 5.8).
  Infection medium: 68.4 g/L sucrose, 36 g/L glucose, N6 salts and vitamins, 1 g/L casein hydrolysate, 0.5 g/L L-proline, 0.5 g/L glutamine, 2 mg/L 2,4-D (pH 5.2). Acetosyringone (AS 100 µM) is added just prior to use.
  Co-cultivation medium: 30 g/L sucrose, 10 g/L glucose, N6 salts and vitamins, 1 g/L casein hydrolysate, 0.5 g/L L-proline, 0.5 g/L glutamine, 2 mg/L 2,4-D, 4 g/L gelrite (pH 5.8). Acetosyringone (AS 100 µM) is added just prior to use.
  Selection medium I: 30 g/L sucrose, N6 salts and vitamins, 1 g/L casein hydrolysate, 0.5 g/L L-proline, 0.5 g/L glutamine, 2 mg/L 2,4-D and 4 g/L gelrite (pH 5.8). 300 mg/L cefotaxime and 50 mg/L hygromycin are added to this medium after autoclaving.
  Selection medium II: 30 g/L sucrose, MS salts and vitamins, 1 g/L casein hydrolysate, 2 mg/L BAP, 0.5 mg/L NAA and 4 g/L gelrite (pH 5.8). 200 mg/L cefotaxime and 50 mg/L hygromycin are added to this medium after autoclaving.

Callus Induction
  Rice seeds are dehusked, pre-rinsed with 70% ethanol for 2 minutes and washed with twice with sterile water. The seeds are then soaked in 0.1% $HgCl_2$ in a 125 ml sterile conical flask and placed on a shaker for 30 minutes. The seeds are washed 5 times with sterile water, dried on sterile filter paper. The surface sterilized seeds are then kept on callus induction medium (15 seeds per plate) and incubated in light at 25° C. After 2-3 weeks, developing callus is visible on the scutellum of the mature seed. Calli are sub-cultured to fresh induction medium and allowed to proliferate.
  *Agrobacterium* infection: A single colony of *Agrobacterium tumefaciens* strain LBA4404 containing the gene cassette is grown in 5 ml YEP medium (5 g/L yeast extract, 10 g/L peptone, 5 g/L NaCl) containing 50 mg/L rifampicin, 100 mg/L kanamycin and used as inoculum for 50 ml overnight culture. Overnight grown *Agrobacterium* culture is adjusted to OD600 0.5 with infection medium. The liquid infection medium is supplemented with 100 µM acetosyringone (AS). The calli are infected with this medium for 1 hour in conical flasks on a shaker (low setting).
  After infection, the bacterial suspension is removed. The calli are blotted dry on sterile filter paper and placed on co-cultivation medium. The calli are co-cultivated in dark at 25° C. for 3 days.
  The infected calli are washed 5 times with sterile water, blotted dry on sterile filter paper and transferred to selection medium containing 300 mg/L cefotaxime and 50 mg/L hygromycin. Election plates are wrapped with parafilm and placed in the light at 25° C. The tissue are subcultured onto fresh selection medium every two weeks. After 6-8 weeks selection the actively growing callus is distinguished from the brown non-transformed tissue.
  The white proliferating calli in presence of hygromycin are transferred to regeneration medium I (in light at 25° C.). After 2-3 weeks, the regenerated shoot buds are transferred to regeneration medium II (in light at 25° C.). The rooted plants are transferred to soil and grown in a green house.

Example 5

SAP Gene Expression in *Arabidopsis*

SAP genes are constitutively expressed in *Arabidopsis* tissues. FIG. 3 shows the PCR amplification of AtSAP11, AtSAP13, AtSAP14, AtSAP12, and AtSAP10, from an *Arabidopsis* flower cDNA library. FIG. 3 also shows the rice OsSAP16 gene product expressed from rice shoot and root cDNA libraries. The PCR products are resolved on 1% agarose gel.

As shown in FIG. 4, AtSAP genes are induced in response to metal or metalloid exposure. FIG. 4 shows a semi-quantitative RT-PCR analysis of *Arabidopsis* AtSAP11, AtSAP13, AtSAP12, and AtSAP10 mRNA expression in root tissue and rice OsSAP16 mRNA expression in root and shoot tissues exposed to As(III), As(V), $Zn^{2+}$, and $Cd^{2+}$ at different time intervals (12 and 24 hours) as compared to controls without any metal treatment. ACT2 and ACT1 genes are used as an equal cDNA amount used for RT-PCR and equal loading controls in *Arabidopsis* and rice, respectively. 250 ng RT-PCR cDNA is used for amplification. PCR cycles numbers and cDNA concentrations are optimized. Preliminary RT-PCR analysis of mRNA corresponding to AtSAP11, AtSAP13, AtSAP12 and AtSAP10 genes from As(III) and As(V) exposed root tissues show AtSAP11, AtSAP12 and AtSAP10 genes are strongly upregulated in response to both As(III) and As(V) after a 12 hour exposure, whereas, AtSAP13 mRNA transcripts are slightly higher than controls (FIG. 4). At 24 hours, the transcript levels decrease almost to the levels similar to controls in AtSAP11 and AtSAP12. Additionally, the mRNA transcript levels of AtSAP12 at 12 and 24 hrs exposure to $Zn^{2+}$ and $Cd^{2+}$ are strongly upregulated in root tissues, slightly upregulated in AtSAP11 and AtSAP13, and mRNA levels are constitutive in AtSAP10 (FIG. 4). For rice OsSAP16, transcript levels are several-fold higher in response to both As(III) and As(V) in root and shoot tissues (FIG. 4).

As shown in FIG. 5, gene expression of AtSAP13 in transgenic lines is confirmed by performing semi-quantitative RT-PCR. The mRNA expression levels in four AtSAP13 transgenic lines are more than two-fold higher as compared to wild type (WT) control plants. Actin 2 (ACT2) is used as an equal loading control.

FIG. 6 shows semi-quantitative RT-PCR analysis of AtSAP10 expression in response to various stress treatments. Expression analysis is performed with AtSAP10 specific primers from the RNA isolated from the *Arabidopsis* seedlings subjected to As(III) and As (V) (A), Cd and Zn (B), Ni (C), Mn (D), ABA (E), Heat (F), Salt (G), and Cold (H) treatments. All upper panels represent AtSAP10 and lower panel represent ACT2 used as internal loading control. Numbers on each upper panel represents time intervals in hours for which the stress treatments are given.

Example 6

Germination and Growth

Wild type (Columbia) and transgenic *Arabidopsis* seeds are sterilized by rinsing in 70% ethanol for 1 minute, then in 30% CLOROX™ bleach (5.25% sodium hypochlorite) for 30 minutes with frequent shaking, followed by 4 rinses in sterile water. Sterilized seeds are sown on one half strength MS medium containing 30 g/liter sucrose, 0.8% PHYTAGAR (purified agar) (GIBCO/BRL, Invitrogen, Carlsbad, Calif.), pH 5.7. The seeds plated on media are vernalized at 4° C. for at least 25 hours. Seedlings are grown at 22° C. with a daily regime of 16 hours light/8 hours darkness. Shoots and roots of three-week old individual seedlings are harvested separately, rinsed with sterile water, dry-blotted, weighed and root length is measured.

Example 7

Metal Resistance of Transgenic *Arabidopsis* Lines

*Arabidopsis* AtSAP13 is expressed under the control of a constitutive promoter (ACT2pt::AtSAP13) in transgenic *Arabidopsis* plants. The transgenic plants are highly resistant to metal concentrations that inhibit growth in wild type control *Arabidopsis*. FIG. 7. For metal resistance assays, transgenic plant lines are grown on ½×MS media supplemented with different metals. For As(III), As(V), Zn and Cd stress treatments, wild type *Arabidopsis* seeds are grown in half strength liquid MS medium in 250 ml flasks under control conditions (16 hours light and 8 hours dark at 22° C. and 18° C., respectively) with constant swirling. After 12 days, plants are exposed to toxic metals by adding sodium arsenite at 25 µM, sodium arsenate at 150 µM, cadmium chloride at 75 µM, and zinc sulfate at 500 µM. Tissue is collected after 0, 12, and 24 hours.

For Ni, Mn, and abscisic acid (ABA) treatments, seeds of wild type plants are germinated on a nylon mesh placed on half-strength MS agar plates. The 12 days old seedlings along with the supporting mesh are transferred on a 2 cm long piece of 50 ml Nalgene plastic tube support placed in the magenta boxes containing half-strength MS liquid medium and allowed to acclimatize for additional period of seven days. At the end of acclimatization period, plants are exposed to Ni, Mn, and ABA by adding 90 µM nickel chloride, 1 mM manganese chloride, 154 and 1.5 µM ABA, 155 respectively. Without being bound by theory, ABA is a phytohormone thought to regulate plant responses to abiotic environmental stresses. Shoot and root tissues are harvested separately after 0, 6, 12, and 24 hours.

For heavy metal tolerance/sensitivity analysis, seeds of the wild type and transgenic plants are germinated and grown on vertically placed half-strength MS agar plates (with 1% sucrose) in the absence or presence of heavy metals for three weeks with a 16 hrs light/8 hrs dark cycle at 22° C./18° C. day/night temperature. To reduce variations, wild type and AtSAP10 plants are grown side by side on the same plate and their growth is compared. Plants are collected, weighed and their root lengths are measured.

Referring to FIG. 7, constitutive expression of an arsenite-inducible putative zinc-finger protein (AtSAP13) from a promoter expression cassette, ACT2pt, confers strong resistance to toxic metals (500 micromolar zinc, 25 micromolar arsenite (As(III)), and 75 micromolar cadmium) in *Arabidopsis*. The T2 homozygous transgenic seeds are grown on ½×MS media supplemented with metal concentrations as indicated and plants are allowed to grow for 3 weeks. The transgenic plants have a fresh or wet weight that is several fold greater than the wild type plants and had well-developed, longer roots. As shown in FIGS. 8-10, transgenic AtSAP10 *Arabidopsis* plants are also resistant to nickel, manganese, and zinc. FIGS. 8-10.

FIG. 8 shows the nickel (Ni) resistance phenotype of *Arabidopsis* AtSAP10 overexpression lines. (A) Ni resistance phenotypes, (B) Fresh shoot weight, and (C) root length of three transgenic lines AtSAP10-23, AtSAP10-30, and AtSAP10-42 overexpressing AtSAP10 from ACT2pt expression cassette and wild type (WT) plants grown on 90 µM $NiCl_2$ in half-strength MS medium for three weeks. The average and standard deviation (SD) values are represented for four replicates of 12 seedlings each for WT and all AtSAP10 lines. The asterisks represent the significant difference in biomass accumulation and root length compared with wild type (WT) plants, (*) $P<0.05$, (**) $P<0.01$.

FIG. 9 shows the manganese (Mn) resistance phenotype of *Arabidopsis* AtSAP10 overexpression lines. (A) Mn resistance phenotypes and (B) Fresh shoot weight of three transgenic lines AtSAP10-23, AtSAP10-30, and AtSAP10-42 overexpressing AtSAP10 from ACT2pt expression cassette and wild type (WT) plants grown on 1 mM $MnCl_2$ in half-strength MS medium 596 for three weeks. The average and standard deviation (SD) values are represented for four replicates of 12 seedlings each for WT and AtSAP10 lines. The asterisks represent the significant difference in biomass accumulation compared with wild type (WT) plants, (*) $P<0.05$, (**) $P<0.01$.

FIG. 10 shows the zinc (Zn) resistance phenotype of *Arabidopsis* AtSAP10 overexpression lines. (A) Zn resistance phenotypes, (B) Fresh shoot weight, and (C) root length of three transgenic lines AtSAP10-23, AtSAP10-30, and AtSAP10-42 overexpressing AtSAP10 from ACT2pt expression cassette and wild type (WT) plants grown on 500 µM $ZnSO_4$ in half-strength MS medium for three weeks. The average and standard deviation (SD) values are represented for four replicates of 12 seedlings each for WT and all AtSAP10 lines. The asterisks represent the significant difference in biomass accumulation and root length compared with wild type (WT) plants, (*) $P<0.05$, (**) $P<0.01$.

These results are unexpected because prior research had demonstrated that the nematode homologue aip-1 is selectively induced by arsenite and zinc but not other metals. Without being bound by theory, it is believed that the $Cys_2$-$His_2$ zinc finger domains in the plant SAP homologues are able to bind several different metals and metalloids and their ions. The protein-metal complexes reduce or eliminate the toxicity of the metal or metalloid. It is further possible that the protein-metal complexes are sequestered in specialized subcellular compartments.

Example 8

Metal Accumulation in Transgenic *Arabidopsis* Lines

For heavy metal accumulation analysis, seeds of wild type and transgenic plants are germinated on a nylon mesh placed on half-strength MS agar plates (with 1% sucrose). The 12 days old seedlings along with the supporting mesh are transferred on a 2 cm long piece of 50 ml Nalgene plastic tube support placed in the magenta boxes containing half-strength MS liquid medium and allowed to acclimate for additional period of seven days. At the end of acclimatization period, the half-strength MS liquid medium is replaced 200 with a new liquid medium containing the appropriate amounts of metals and are continued to grow for another four days. At the end of fourth day, plants are removed from the magenta boxes, harvested root and shoot separately, washed three to four times with Mili-Q water and dried in paper folds at 70° C. for 48 hours. Dried plant samples are crushed to fine powder, weighed, and then digested in the concentrated nitric acid (10 mg/ml) with constant shaking for 48 hours. Hydrogen peroxide (30%) is added at the end of 48 hrs of acid digestion to promote oxidation of organic matter and achieve complete digestion. Samples are then centrifuged at 3000 rpm for 10 min and the clear supernatant is diluted 10-fold with deionized water. Samples are analyzed by Elan DRCe inductively coupled plasma-mass spectrometry (ICP-MS).

To analyze the uptake of arsenic (As), cadmium (Cd), and zinc (Zn) in the root and shoot tissues of transgenic plants overexpressing AtSAP13, independent transgenic lines are grown on ½×MS media containing 25 millimolar As(III) and 400 millimolar Zn for three weeks. Plant tissues are harvested, washed, acid digested and metal contents are analyzed by ICP-MS. The levels of arsenic in these transgenic lines are similar to the control plants, whereas, the transgenic lines accumulated significantly higher levels of zinc in both root and shoot tissues as compared to wild type controls (FIG. 11). The overexpression of AtSAP13 gene in transgenic plants caused significant increased accumulation of zinc in plant tissues without increasing toxic arsenic accumulation. Zinc is a required, but often deficient, nutrient for plants. Therefore, overexpression of the SAP genes in plants and increased zinc accumulation is highly desirable for crop improvement.

FIG. 12 shows the total Ni, Mn, and Zn accumulation in *Arabidopsis* SAP10 overexpression lines. The total Ni concentration in shoots (A) and roots (B) of wild type (WT) and four overexpression lines of AtSAP10 grown on hydroponics medium containing 90 µM $NiCl_2$. Total Mn accumulation in shoots (C) and roots (D) of wild type (WT) and four overexpression transgenic lines of AtSAP10 grown on hydroponics medium containing 1 mM $MnCl_2$. Total Zn accumulation in shoots (E) and roots (F) of wild type (WT) and four overexpression transgenic lines of AtSAP10 grown on hydroponics medium containing 500 µM $ZnSO_4$. The average and standard deviation (SD) values are shown for four replicates of 25 plants each for WT and all AtSAP10 lines. Asterisk represents the significant difference in Ni, Mn, or Zn accumulation as compared to wild type (WT), (*)<0.05, (**)<0.01.

Example 9

Abiotic Stress Resistance of Transgenic *Arabidopsis* Lines

The AtACR2 transgenic plants are also resistant to salt, drought, and cold stress. Three-week old transgenic plants are grown on 250 millimolar NaCl for one week and show strong resistance to salt as compared to control wild type plants. As shown in FIG. 13, constitutive expression of AtSAP13 from a promoter expression cassette, ACT2pt, conferred strong resistance to high salt concentration in *Arabidopsis*. After the one week salt treatment, the wild type plant died, whereas the transgenic plants recovered from the salt stress and grew well. Further, these plants are subjected to drought (withholding watering for 8 days and then recovery with watering) and cold temperature (2° C. for 5 days). Preliminary results indicate that AtACR2 plants transgenic plants show increased resistance to both stresses.

For heat treatment, magenta boxes containing wild type plants are kept in an incubator at 38° C. for 0.5, 1, 3, and 6 hours. For cold treatment, magenta boxes with wild type plants are transferred to a growth chamber maintained at 2° C. for 0.5, 1, 3, and 6 hours. Drought stress is tested by removing plants from magenta boxes and placing them on a dry paper towel to remove any excess adhered nutrient solution. Plants are air dried by transferring into dry magenta boxes for the desired time points. Plants are exposed to salt stress by replacing normal half-strength MS medium with medium supplemented with 150 mM sodium chloride for desired time points. All samples are harvested, washed with deionized water, and stored at −80° C. until further use.

High temperature stress tests are performed by growing wild type and transgenic plants side by side on half-strength MS agar plates (with 1% sucrose) with a 16-hour light/8-hour dark cycle at 22° C./18° C. light/dark temperatures for 12 days. The seedlings are initially exposed to 38° C. for 90 minutes and then left at room temperature (22° C.) for 120 minutes before finally being exposed to 45° C. for 1 hour. All heat treatments are performed in the dark. Plants are allowed to recover in a growth chamber for 6 days with a 16-hour light/8-hour dark cycle at 22° C./18° C. At the end of the sixth day, plants are again heat shocked at 45° C. for 3 hours and then placed in a growth chamber for a 5-day recovery period before scoring.

FIG. 14 shows the effect of high temperature stress on wild type (WT) and AtSAP10 overexpression transgenic lines. 12-day old seedlings are heat stressed (HS) as described above. Photographs of representative plates containing WT and AtSAP10 transgenic lines are taken after 5 days of recovery.

FIG. 15 shows the effect of drought on wild type (WT) and AtSAP13 overexpression transgenic lines. *Arabidopsis* plants overexpressing AtSAP13 exhibited drought tolerance. Transgenic *Arabidopsis* plants overexpressing AtSAP13 remained healthy, whereas, wild type plants died under drought stress. Plants were grown in well-watered soil for 25 days and then water was withhold for 11 days.

A transgenic plant comprising a recombinant plant SAP coding sequence operatively linked to a plant-expressible transcription regulatory sequence will advantageously provide improved environmental stress resistance in plants such as crop plants and other economically important plants. The environmental stress resistant transgenic plant will also advantageously increase crop yield. The environmental stress resistant transgenic plant will further provide increased plant biomass. The improved environmental stress resistance, increased crop yield, and increased plant biomass will also be highly advantageous in biofuel applications.

The terms "first," "second," and the like, "primary," "secondary," and the like, as used herein do not denote any order, quantity, or importance, but rather are used to distinguish one element from another. The terms "a" and "an" do not denote a limitation of quantity, but rather denote the presence of at least one of the referenced item.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A transgenic plant transformed with an isolated nucleic acid comprising a plant arsenite-inducible RNA-associated protein coding sequence operatively linked to a plant-expressible transcription regulatory sequence, wherein the plant arsenite-inducible RNA-associated protein coding sequence encodes a polypeptide that is at least 95% identical to a polypeptide sequence selected from the group consisting of SEQ ID NO:8, SEQ ID NO:9, SEQ ID NO:10, SEQ ID NO:11, SEQ ID NO:12, SEQ ID NO:13, and SEQ ID NO:14, wherein the plant arsenite-inducible RNA-associated protein coding sequence encodes a polypeptide that confers resistance to an environmental stress,
wherein greater than or equal to about 25% of transgenic plants are resistant to an environmental stress, and wherein the environmental stress inhibits the growth of wild type plants.

2. The transgenic plant of claim 1, wherein the transgenic plant is selected from the group consisting of *Arabidopsis thaliana*, canola, sunflower, tobacco, switchgrass, *Brachypodium*, mustard, crambe, sugar beet, cotton, maize, wheat, barley, rice, sorghum, mangel-wurzels, tomato, mango, peach, apple, pear, strawberry, banana, melon, potato, carrot, lettuce, cabbage, onion, soybean, sugar cane, pea, field beans, poplar, grape, citrus, alfalfa, rye, oats, turf and forage grasses, biofuel, biomass, and bioenergy crop plants, flax, camolina, and oilseed rape, and nut producing plants.

3. The transgenic plant of claim 1, wherein the environmental stress is a metal, metal ion, metalloid, metalloid ion, salinity, drought, cold, heat, submergence, or a combination comprising one of the foregoing.

4. The transgenic plant of claim 1, wherein the transgenic plant is *Arabidopsis thaliana* or rice.

5. The transgenic plant of claim 1, wherein the plant arsenite-inducible RNA-associated protein coding sequence is derived from *Arabidopsis thaliana* or rice.

6. The transgenic plant of claim 1, wherein the plant arsenite-inducible RNA-associated protein coding sequence is selected from the group consisting of SEQ ID NO:1, SEQ ID NO:2, SEQ ID NO:3, SEQ ID NO:4, SEQ ID NO:5, SEQ ID NO:6, and SEQ ID NO:7.

7. The transgenic plant of claim 1, wherein the plant-expressible transcription regulatory sequence comprises a constitutive promoter, an inducible promoter, a tissue-specific promoter, an organ-specific promoter, or a combination of one or more of the foregoing promoters.

8. The transgenic plant of claim 7, wherein the constitutive promoter is a plant ACT2 promoter or a plant ACT1 promoter.

9. The transgenic plant of claim 2, wherein the metal, metal ion, metalloid, or metalloid ion is arsenic, arsenate, arsenite, cadmium, chromium, lead, manganese, mercury, nickel, zinc, or a combination comprising one of the foregoing.

10. The transgenic plant of claim 2, wherein the metal, metal ion, metalloid, or metalloid ion is arsenic, arsenate, arsenite, cadmium, manganese, nickel, or zinc.

11. The transgenic plant of claim 1, wherein abscisic acid regulates the plant response to the environmental stress.

12. The transgenic plant of claim 1, wherein the transgenic plant has a biomass that is greater than or equal to about 100% of the biomass of a wild type plant.

13. The transgenic plant of claim 1, further comprising an isolated nucleic acid comprising a phytochelatin biosynthetic enzyme coding sequence that is greater than or equal to about 95% homologous with a sequence selected from the group consisting of SEQ ID NO:18, SEQ ID NO:19, and SEQ ID NO:20, wherein the phytochelatin biosynthetic enzyme coding sequence has phytochelatin biosynthesis activity.

14. A method for producing a transgenic plant that is resistant to an environmental stress comprising
introducing an isolated nucleic acid comprising an plant arsenite-inducible RNA-associated protein coding sequence that encodes a polypeptide that is at least 95% identical to a polypeptide sequence selected from the group consisting of SEQ ID NO:8, SEQ ID NO:9, SEQ ID NO:10, SEQ ID NO:11, SEQ ID NO:12, SEQ ID NO:13, and SEQ ID NO:14 operatively linked to a plant-expressible transcription regulatory sequence into a plant cell or plant tissue;
producing a transgenic plant cell or tissue comprising the isolated nucleic acid; and
regenerating the transgenic plant cell or transgenic plant tissue to provide a transgenic plant that is resistant to an environmental stress,
wherein greater than or equal to about 25% of transgenic plants are resistant to the environmental stress, and wherein the environmental stress inhibits the growth of wild type plants.

15. The method of claim 14, wherein the environmental stress is a metal, metal ion, metalloid, metalloid ion, salinity, drought, cold, heat, submergence, or a combination comprising one of the foregoing.

16. The method of claim 14, wherein the transgenic plant is *Arabidopsis thaliana* or rice.

17. The method of claim 14, wherein the plant-expressible transcription regulatory sequence comprises a constitutive promoter, an inducible promoter, a tissue-specific promoter, an organ-specific promoter, or a combination of one or more of the foregoing promoters.

18. The method of claim 14, wherein the plant arsenite-inducible RNA-associated protein coding sequence is selected from the group consisting of SEQ ID NO:1, SEQ ID NO:2, SEQ ID NO:3, SEQ ID NO:4, SEQ ID NO:5, SEQ ID NO:6, and SEQ ID NO:7.

19. The method of claim 15, wherein the metal, metal ion, metalloid, or metalloid ion is arsenic, arsenate, arsenite, cadmium, chromium, lead, manganese, mercury, nickel, zinc, or a combination comprising one of the foregoing.

20. The method of claim 15, wherein the metal, metal ion, metalloid, or metalloid ion is arsenic, arsenate, arsenite, cadmium, manganese, nickel, or zinc.

* * * * *